United States Patent
Turner et al.

(10) Patent No.: US 9,938,562 B2
(45) Date of Patent: *Apr. 10, 2018

(54) NAPHTHALENE DERIVED CHROMOGENIC ENZYME SUBSTRATES

(71) Applicant: Glycosynth Limited, Warrington cheshire (GB)

(72) Inventors: Hayley Jane Turner, Warrington (GB); Michael Burton, Warrington (GB)

(73) Assignee: GLYCOSYNTH LIMITED (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/035,152

(22) PCT Filed: Nov. 3, 2014

(86) PCT No.: PCT/GB2014/053260
§ 371 (c)(1),
(2) Date: May 6, 2016

(87) PCT Pub. No.: WO2015/067927
PCT Pub. Date: May 14, 2015

(65) Prior Publication Data
US 2016/0298167 A1    Oct. 13, 2016

(30) Foreign Application Priority Data
Nov. 8, 2013 (GB) .................. 1319768.6

(51) Int. Cl.
*C12Q 1/34* (2006.01)
*C07H 15/20* (2006.01)
*C07H 15/203* (2006.01)

(52) U.S. Cl.
CPC .............. *C12Q 1/34* (2013.01); *C07H 15/20* (2013.01); *C07H 15/203* (2013.01); *G01N 2333/938* (2013.01)

(58) Field of Classification Search
None
See application file for complete search history.

(56) References Cited

U.S. PATENT DOCUMENTS

| | | | |
|---|---|---|---|
| 5,219,922 A | 6/1993 | Steinberger et al. | |
| 5,358,854 A | 10/1994 | Ferguson | |
| 5,861,270 A | 1/1999 | Nelis | |
| 6,008,008 A | 12/1999 | James et al. | |
| 7,052,863 B2 | 5/2006 | Armstrong et al. | |
| 7,563,592 B2 | 7/2009 | Armstrong et al. | |
| 8,216,802 B2 | 7/2012 | Casse et al. | |
| 8,334,112 B2 | 12/2012 | Monget et al. | |
| 2001/0027947 A1* | 10/2001 | Tsuchiya | B09C 1/10 210/601 |
| 2012/0148516 A1* | 6/2012 | Abel | A61Q 17/00 424/62 |

FOREIGN PATENT DOCUMENTS

| | | |
|---|---|---|
| EP | 1438423 | 7/2004 |
| EP | 1438424 | 7/2004 |
| EP | 2256103 | 12/2010 |
| GB | 2022276 | 12/1979 |
| JP | 2004224762 | 8/2004 |
| JP | 2004224763 | 8/2004 |
| WO | 9304077 | 3/1993 |
| WO | 2008004788 | 1/2008 |
| WO | 2012168415 | 12/2012 |

OTHER PUBLICATIONS

English translation of JP 2004224762 published Aug. 12, 2004.*
Siloniz et al. J. Food protection (2000) 63(5): 651-654.*
Baron, A.S. et al., Mg1A and Mg1B are required for the intramacrophage growth of Francisella novicida, Mol. Microbiol., 29, 247-259, (1998).
Bhowmik, et al., A novel "pro-sensitizer" based sensing of enzymes using Tb(III) luminescence in a hydrogel matrix, Chem. Commun., 48, 4624-4626, (2012).
Binder, et al., Bile acid inhibition of intestinal anaerobic organisms, Amer. J. Clin. Nutr., 28, 119-125, (1975).
Bollenback, G.N. et al, J. Am. Chem. Soc., 77, 3310, (1955).
Brenner, K.P. et al, New medium for the simultaneous detection of total coliforms and *Escherichia coli* in water, Appl. Environ. Microbiol., 59, 3534-3544, (1993).
Butterworth, L. et al., Evaluation of novel beta-ribosidase substrates for the differentiation of Gram-negative bacteria, J. Appl. Microbiol., 96, 170-176, (2004).
Chiu-Machado, I. et al, Bile acid inhibition of intestinal anaerobic organisms, J. Carb. Chem., 14, 551, (1995).
Floch et al, The effect of bile acids on intestinal microflora, Amer. J. Clin. Nutr., 25, 1418-1426, (1972).
Jacobsson, M. et al., Synthesis of naphthoxylosides on solid support, Tetrahedron Letters, 43, 6549-6552, (2002).
James, A.L. et al, Evaluation of p-Naphtholbenzein-b-D-Galactoside as a Substratefor Bacterial b-Galactosidase, Applied and Environmental Microbiology 66: 5521-5523, (2000).
James, A.L. et al, Alizarin-beta-D-galactoside: a new substrate for the detection of bacterial beta-galactosidase, Letters Appl. Microbiol., 30:336-340, (2000).

(Continued)

*Primary Examiner* — Susan Hanley
(74) *Attorney, Agent, or Firm* — Christopher M. Scherer; Daniel A. Blasiole; DeWitt Ross & Stevens S.C.

(57) ABSTRACT

Conjugates of 2,3-dihydroxynaphthalene and its derivatives with enzyme cleavable groups are chromogenic substrates that form colored compounds when complexed with metal ions, e.g. iron ions, on cleavage by enzymes, and are useful in microbial detection and identification. The cleavage products form purple or red-brown colored complexes, that can easily be observed by the naked eye. Microbes can be grown in the presence of the substrates and the metal salts that provide the metal ion for complexing with the 2,3-dihydroxynaphthalene product. Substituents in the naphthalene ring may affect the solubility of the substrates and also the diffusibility and color of the metal complexes. Some of the substrates yield soluble complexes on cleavage and are of particular value in liquid growth media. Other substrates produce less soluble complexes that are more suitable for use in solid agar media. Methods of synthesizing the substrates are described.

15 Claims, No Drawings

(56) References Cited

OTHER PUBLICATIONS

Johnsson, R. et al., Synthesis and biology of bis-xylosylated dihydroxynaphthalenes, Bioorganic and Medicinal Chemistry, 15, 2868-2877, (2007).
Kurdi, et al, Mechanism of growth inhibition by free bile acids in lactobacilli and bifidobacterial, J. Bacteriol., 188, 1979-1986, (2006).
Patrovsky, V., 2,3-Dihydroxynaphthalin als neues Reagenz zur extraktiven photometrischen Bestimmung von Eisen-, Vanadin-, Titan- und Molybdänspuren, Coll. Czech. Chem. Commun., 35, 1599-1604, (1970) (Abstract Only).
Perry, J.D. et al., ABC medium, a new chromogenic agar for selective isolation of *Salmonella* spp, J. Clin. Microbiol., 37, 766-768, (1999).
Perry, J.D. et al., Evaluation of novel chromogenic substrates for the detection of bacterial beta-glucosidase, J. Appl. Microbiol., 102, 410-415, (2006).
Reinders, R.D. et al, Use of 8-Hydroxyquinoline-β-d-glucuronide for presumptive identification of Shiga toxin-producing *Escherichia coli* O157, Lett. Appl. Microbiol., 30, 411-414, (2000).
Swan, A., The use of a bile-aesculin medium and of Maxted's Technique of Lancefield Grouping in the identification of Enterococci (Group D Streptococci), J. Clin. Path., 7, 160-163, (1954).
Tarafder, P.K. et al., A review on the complex forming ability of O-O' type ligands with transition metals: introducing 2,3-dihydroxynaphthalene as a potential analytical reagent, Rev. Anal. Chem., 30, 73-81, (2011).
Van Poucke, S.O. et al., A 210-min solid phase cytometry test for the enumeration of *Escherichia coli* in drinking water, J. Appl. Microbiol., 89,390-396, (2000).
Zincke, T. et al., Annalen, 334, 365, (1904).
Bogdanova et al., "2,2,2-Tribromonaphtho[2,3-*d*] -1,3,2-Dioxaphosphole: Obtaining and Reaction with Phenylacetylene," Phosphorus Sulfur and the Related Elements, Jun. 20, 2008, 183(2-3):650-651.
Kuehl et al., "Determination of Kow Values for a Series of Aryl Glucuronides," Bulletin of Environmental Contamination and Toxicoogy, Jul. 1, 1999, 63(1):109-116.
International Search Report and Written Opinion for PCT/GB2014/053260 dated Jan. 26, 2015.

\* cited by examiner

NAPHTHALENE DERIVED CHROMOGENIC ENZYME SUBSTRATES

CROSS REFERENCE TO RELATED APPLICATIONS

The present application is the U.S. national stage application of International Application PCT/GB2014/053260, filed Nov. 3, 2014, which international application was published on May 14, 2015, as International Publication WO2015/067927. The International Application claims priority of British Patent Application 1319768.6 filed Nov. 8, 2013, the contents of which are incorporated herein by reference in their entireties.

FIELD OF USE

This invention concerns the application of artificial chromogenic enzyme substrates for the detection and identification of microorganisms.

BACKGROUND TO THE INVENTION

Most artificial substrates for hydrolytic enzymes in current large-scale applications in diagnostic microbiology are either chromogenic or fluorogenic. Fluorogenic assays suffer from certain disadvantages, including intrinsic background fluorescence from certain samples. However, perhaps their main disadvantage is the need to use a lamp or other source of UV light to generate the fluorescence. Chromogenic enzyme substrates have an advantage in that the endpoint can be determined with the naked eye. Alternatively, the released chromogen may be assayed using simple spectrophotometers working by absorption of light in the visible wavelengths. For an enzyme substrate to be of real value in diagnostic microbiology, certain conditions need to be met. When attached to the target residue (i.e. a sugar, ester or phosphate) the artificial enzyme substrates should be practically colourless or have a very low background colouration that does not interfere significantly with the test procedure. However, once cleaved from the target portion by enzymatic hydrolysis, the free core molecule is either highly coloured or can be converted to a coloured compound in situ by further chemical (i.e., non-enzymatic) reaction. Ideally, this reaction should be virtually instantaneous with the enzymatic cleavage and the conditions or reagents required to produce the colour should preferably be already present in the media, and therefore must be able to allow adequate microbial growth. Under these conditions, the presence of the coloured end-product gives a good indication of the enzyme activity targeted. The substrates should be convenient to synthesise from inexpensive starting materials so that many different substrates can be produced from the same core molecule; they should be easy to use, suitable for continuous assays, and they should be able to work under both aerobic and anaerobic conditions. Although not a prerequisite for ultimate utility, it would be a further advantage if the chromogen was contrasting in colour to the chromogens of currently available enzyme substrates. In liquid media the chromogen should be largely soluble. In solid or gelled plate media (such as the commonly used agar plates) the chromogen should be non-diffusible so that the colour remains concentrated in the colony mass. In agar tube media, diffusion of the chromogen is acceptable.

Many different artificial chromogenic enzyme substrates derived from various core molecules have been produced and are currently commercially available. However, all core molecules have limitations as well as advantages depending upon the specific application. Some of the positive and negative attributes of the main types of chromogenic enzyme substrates employed to detect glycosidase activities may be set out as follows.

Nitrophenyl substrates are widely employed in liquid media. One common example, o-nitrophenyl-β-D-galactopyranoside (ONPG), is cheap and easy to use. However, in agar plate media diffusion of the yellow o-nitrophenol chromogen makes it impractical to detect enzyme-positive from enzyme-negative cultures of microorganisms in a polymicrobial culture. A further disadvantage is that the pale yellow colour given after hydrolysis is not dissimilar to the background colour already present in certain culture media. Moreover, the maximum colour of o-nitrophenol is only generated at highly alkaline pH at which most microorganisms will not grow. p-Nitrophenyl-β-D-glucuronide is an enzyme substrate that has been used to detect β-D-glucuronidase from E. coli and thereby identify this bacterium, but the yellow p-nitrophenol shares all the defects of its isomer o-nitrophenol. Phenolphthalein is another inexpensive core molecule of some chromogenic enzyme substrates. As with the nitrophenols, the phenolphthalein aglycone diffuses greatly in agar media. Moreover, the free phenolphthalein has to be made highly basic before the red colour develops, so phenolphthalein substrates are unsuitable for continuous assays. Although this core molecule is inexpensive, its glycosides, such as phenolphthalein-β-D-glucuronide, are very expensive, undoubtedly because of difficulties with their synthesis. For all the above reasons, phenol phthalein-derived enzyme substrates are little used currently. Resorufin is a very costly core molecule that is both chromogenic and fluorogenic; the few commercially available glycosides derived from it are thus very expensive. Resorufin substrates are suitable for liquid media only.

For use in solid media (agar plates) and other situations in which an essentially insoluble or non-diffusible chromogenic endpoint is required, indoxyl substrates tend to be preferred, X-Gal (5-bromo-4-chloro-3-indolyl-β-D-galactopyranoside) is a common example. On enzymatic cleavage, oxidation of 5-bromo-4-chloroindoxyl in situ yields a bright blue-green insoluble indigo dye that will stay localised within microbial colonies, thereby affording good differentiation of colonies within a polymicrobial culture on agar plates. X-β-D-glucuronide is extensively used in microbiological media to detect E. coli. A whole range of differently substituted indoxyl glycosides, carboxylic acid esters and phosphates is commercially available. The use of different coloured indoxyl substrates in the same medium has been exploited for the simultaneous detection of two or more different enzyme activities [J. N. Roth and W. J. Ferguson, U.S. Pat. No. 5,219,922, (1993); W. J. Ferguson, U.S. Pat. No. 5,358,854, (1994)]. Negative aspects of indoxyl substrates are that they are not well suited to liquid media and that the indigo dye can only be generated under oxidative conditions. This last property makes them unsuited to the detection of anaerobes and is a severe limitation when dealing with this type of organism. Indoxyl substrates have also been shown to exhibit toxicity to bacteria as evidenced by the formation of small colonies [A. S. Baron and F. E. Nano, Mol. Microbiol., 29, 247-259, (1998); L. Butterworth et al, J. Appl. Microbiol., 96, 170-176, (2004)]. Typically, indoxyl substrates are more expensive than their nitrophenyl counterparts; X-Gal is approximately one order of magnitude more expensive than ONPG in bulk.

Enzyme substrates derived from 1-naphthol, 2-naphthol, and compounds in the naphthol-AS series are known. The released naphthols are not themselves chromogenic, and a diazonium salt has to be added to produce the insoluble dye. The need to add a coupling reagent post-incubation renders these substrates unsuitable for continuous assay as well as greatly adding to the inconvenience of any test. Above all, diazonium salts are to be avoided for routine work because of their general toxicity.

James and co-workers [A. L. James et al, Applied and Environmental Microbiology, 66, 5521-5523, (2000)] synthesised the novel chromogenic substrate p-naphtholbenzein-β-D-galactopyranoside for use in solid plate media. Bacterial hydrolysis of this substrate gave pink, non-diffusible colonies. The principle on which this aglycone works appears to be its large size combined with its hydrophobic nature. Its sensitivity when challenged with nearly 400 bacterial strains was lower than X-Gal. This may explain why the substrate is not commercially available and why other glycosides of p-naphtholbenzein have not so far been reported.

Recently, substrates generating their colour via intermolecular or intramolecular aldol reactions have been disclosed [U. Spitz et al, EP 20090159639, (2009)]. Although a number of advantages are claimed for these Aldol substrates, their synthesis actually starts from other indoxyls substrates, thus making them potentially very expensive. Another disadvantage of their synthesis is that some examples require the preparation and use of some reagents not commercially available.

Artificial chromogenic enzyme substrates based on metal chelation are well-known. Glycosides of 8-hydroxyquinoline generate insoluble coloured iron chelates after release of the aglycone. A commercial medium using 8-hydroxyquinoline-β-D-glucuronide has been evaluated [R. D. Reinders et al, Lett. Appl. Microbiol., 30, 411-414, (2000)], but for bacterial diagnosis a restricting factor is the toxicity of the aglycone to Gram-positive organisms [J. D. Perry et al, J. Appl. Microbiol., 102, 410-415, (2007)]. The range of 8-hydroxyquinoline substrates commercially available is limited, possibly on account of difficulties in their synthesis, and the substrates are unsuited to liquid media. However, most of the artificial enzyme substrates described as working via metal chelation are composed of core molecules that contain an ortho-dihydroxyaromatic system. Many different compounds containing the ortho-dihydroxyaromatic system have been described as metal chelators, and they form coloured complexes with a wide variety of metal ions depending on the compound and the metal ion in question. Nevertheless, the first chromogenic chelating-type enzyme substrate containing an ortho-dihydroxyaromatic moiety to be used was a natural compound, esculin. Esculin is the β-D-glucopyranoside of esculetin. Used with an iron salt, esculin finds employment as a reagent for Group D streptococci [A. Swan, J. Clin. Path., 7, 160-163, (1954)]. Unfortunately, extensive diffusion of the esculetin-iron chromogen presents a problem on agar plate media. The core molecule esculetin is expensive, and this has undoubtedly blocked the commercial development of further glycosides made from it. Therefore esculetin glycosides are not ideal substrates.

In order to address some of the aforementioned limitations of both the indoxyl enzyme substrates and the existing substrates working by metal chelation, James and Armstrong devised novel chromogenic enzyme substrates, the lead core molecule being cyclohexenoesculetin (CHE) [A. L. James and L. Armstrong, U.S. Pat. No. 6,008,008, (1999)]. CHE contains the ortho-dihydroxyaromatic moiety. CHE substrates present no diffusion, and employing them to detect bacteria on solid plate media produces discrete black colonies in the presence of iron, which greatly assists in identification in mixed cultures. CHE enzyme substrates have no background coloration, do not show any measurable toxicity to microorganisms and they can be used under both anaerobic and aerobic conditions. The intense black colour of the CHE-iron chelate may even be used to good effect to mask the colour generated by indoxyl substrates, depending on the circumstances [J. D. Perry et al, J. Clin. Microbiol., 37, 766-768, (1999)]. One disadvantage of CHE glycosides is the relative expense of synthesising CHE itself. Metal chelating-type enzyme substrates with the ortho-dihydroxyaromatic system have also been made from the well-known dye alizarin [L. Armstrong and A. James, U.S. Pat. No. 7,052,863 (2006) and U.S. Pat. No. 7,563,592 (2009)]. Alizarin-β-D-galactopyranoside was shown to be a highly sensitive substrate in agar plate media with an optimal concentration just over half that of X-Gal in the application studied, and this concentration was very much less than that required for the galactosides of CHE and 8-hydroxyquinoline [A. L. James et al, Letters Appl. Microbiol., 30, 336, (2000)]. Another useful attribute of this substrate is its ability to form different colours of chelate depending on the metal ion used. In agar media, alizarin substrates give a violet colour with iron and a bright pink chelate with aluminium. However, the toxicity of alizarin gives rise to small colonies [J. D. Perry et al, J. Appl. Microbiol., 102, 410 (2006)].

Yet a further class of enzyme substrates employing metal chelation with an ortho-dihydroxyaromatic system has been disclosed [M. Burton, EP 1438423, (2007)]. The essence of these substrates is that the ortho-dihydroxybenzene ring is not fused to any other ring system, therefore they are catechols. Other groups (if any) are attached to the catechol ring by single bonds. Substrates of the parent compound, catechol itself, generate a fairly intense black chelate in the presence of iron salts after enzymatic hydrolysis, although this chelate is prone to diffuse in agar media. Catechol β-D-ribofuranoside was demonstrated as an effective enzyme substrate for the revelation of R-D-ribofuranosidase activity in *Shigella* and *Salmonella*, but diffusion of the chromogen would appear to limit its use on agar plate media. The catechol-derivative 3',4'-dihydroxyflavone (DHF) affords substrates showing little or no diffusion in agar media. Like CHE, DHF substrates yield dark brown or black iron chelates with iron salts, but they show some advantage over CHE substrates in that they can form a yellow, non-diffusible chelate with aluminium salts. DHF substrates are essentially non-toxic to microorganisms, but the DHF aglycone is difficult to synthesise and, although it is commercially available, it is very expensive.

WO2008/004788 discloses the synthesis of the dicaprylate of 2,3-dihydroxynaphthalene (DHN). The compounds are said to have potential therapeutic utility for treating the skin disease caused by excessive production of melanin.

Bogdanov et al in Phosphorous, Sulphur and Silicon (2008) 183:650-651 describe synthesis of monophosphate esters of DHN and a ring brominated analogue. Uses of the esters are not disclosed.

GB2022267 discloses DHN conjugates for use in photography in conjunction with chromogenic compounds. The DHN conjugates may decompose under the action of thermal energy, or by reaction with gaseous or liquid chemicals, to then react with the chromogenic compounds to form a coloured image.

At the present time, there is no class of chromogenic enzyme substrates that is inexpensive and simple to prepare, is easy to use, and is suitable for continuous assays of microorganisms in both liquid and solid media, and under both aerobic and anaerobic conditions.

SUMMARY OF THE INVENTION

This invention relates to the use of chromogenic enzyme substrates where the core molecule is provided by 2,3-dihydroxynaphthalene (DHN) and some of its simple derivatives.

According to the first aspect of the present invention, there is provided a new method of detecting target enzyme activity in a medium comprising the steps:
a) contacting a metal compound and an enzyme substrate of the general formula I with a substance suspected of containing or producing said target enzyme

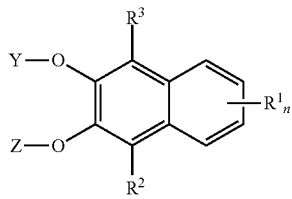

I wherein Y is an enzyme cleavable group;
Z is H, or a metal cation or non-metal cation, acyl or the same enzyme cleavable group as Y;
$R^2$ and $R^3$ are each independent selected from the group consisting of H, OH, $C_1$-$C_8$ alkyl, $C_2$-$C_{24}$ acyl, halogen and nitro, provided that if Z is H or a salt, then $R^2$ must not be OH;
$R^1$ is $C_1$-$C_8$ alkyl, halogen, $NO_2$, $C_2$-$C_{24}$ acyl, OH or —$SO_3X$, where X is H, a metal ion or a non-metal cation;
n is 0-4;
such that a product of enzymatic substrate cleavage is capable of chelating the metal ion of the said metal compound, thereby forming a coloured compound; and
b) detecting the presence of the coloured compound.

According to a second aspect of the present invention a new composition for microbial growth contains the substrate of formula I, the metal compound as defined above and microbial growth nutrients. The compositions may be growth media, or may be added to other components, or alternatively diluted with water or buffer, to form the microbial growth medium.

According to a third aspect of the invention, the composition containing a mixture of the substrate of formula I and an iron compound is believed to be new. This preferred composition may be added to other chromogenic microbial growth medium to form a suitable medium for growing microbes to detect the presence of the selected enzyme activity. Alternatively, the mixture may have other utilities, for instance in chromogenic analysis of enzymes not requiring microbial growth in the presence of the substrate, or to contact samples believed to contain said enzymes from a microbial or non-microbial source.

In the above aspects of the invention, the right hand ring of the 2,3-dihydroxynaphthalene (DHN) core may be unsubstituted, i.e. n is 0. In other embodiments n is 1 and the substituent $R^1$ confers useful (increased or decreased) solubility or diffusibility characteristics. To provide increased water solubility, particularly useful for substrates for lipase and esterase which may otherwise be relatively hydrophobic. $R^1$ may be $SO_3X$ where X is H or $M^{p+}_{1/p}$, wherein p is 1, 2 or 3, and $M^{p+}$ is a metal ion. Preferably, M is Na, K or Rb (and p is 1). Alternatively $M^{p+}$ may be an alkaline earth metal, i.e. p is 2. To provide reduced solubility, or diffusibility in solid media the ring may be substituted by bromine atoms, and/or $R^2$ and $R^3$ may be bromine.

The cleavable group Y is selected according to the target enzyme. For glycosidase targets the group is a glycosyl group, such as a glucosyl, ribofuranosyl, galactosyl or glucuronyl. For phosphatase, the group is phosphate. For lipase or esterase the group is an acyl group such as a $C_{2-24}$ acyl, for instance capryl. A glucuronyl group may be in the form of the free acid or an ester, or in the salt form with a metal cation or non-metal cation. Non-metal cations encompass inorganic cations, such as $NH^+_4$, and organic cations.

The group Z may also be enzyme cleavable, in which case it is usually the same as Y. Acyl ester substrates for lipases and esterases may be di-substituted, for instance. Where Z is acyl and is a different group to Y, it will need to be cleaved in order for the DHN product to chelate the metal ion and form the coloured compound. Such a cleavage reaction may be enzymatic or non-enzymatic.

The metal compound is selected to have a metal ion which forms a coloured compound (believed to be a coordination complex) with the cleavage product (and which is not coloured or is distinguishably coloured from that complex). The metal compound is preferably non-toxic for microorganisms, so that, where the test method involves a step of incubating a sample to allow growth of microorganisms, this step may be carried out in the presence of the metal compound. Alternatively the metal compound may be added later.

The composition of the invention may itself be a growth medium or may be a premix for adding to a growth medium, or a concentrate from which a growth medium, usually a liquid growth medium, may be formed, e.g. by dilution.

The medium generally contains nutrients for microbial growth, growth promoters, growth inhibitors and/or other substrates, preferably chromogenic substrates, for other microbial enzymes. We have found that the enzyme substrates defined herein and their cleavage products allow microbes to grow so that microbial growth can be carried out in the presence of those compounds. The metal compound is also selected for its compatibility with microbial growth. It is thus not necessary for either the substrate or metal compound to be added after a sample has been incubated such that putative enzyme activity is generated upon microbial growth. Rather the incubation medium can contain both compounds at the start of incubation.

The growth medium in some aspects of the present invention is a liquid growth medium, i.e. any medium that is suitable for microbial growth. In this specification reference to liquid means liquid according to the conventional sense of the word, and would be understood by the skilled person to mean free flowing or capable of being poured. In this context liquid media can also refer to viscous liquids, viscosified to provide easier handling and resistance to spillage from the incubation vessel in such an assay. Such viscosity can result from, for example, the addition of agar or other gelling agents in amounts too low to form conventional plate media. Concentrations of agar less than 0.5% should be effective in the liquid media used in the present invention.

The above method is distinguished from plate assays in that it is unnecessary to pinpoint individual colonies, and therefore the medium is not required to be so solid as to maintain colonies in a single orientation.

The present invention may also be used for solid microbial growth media, such as agar gel plate media, whereon pinpoint colonies are maintained and may be incubated upside down because the concentration of agar is sufficient to create and maintain a firm gel.

The microbes for which the present invention is particularly suited, generally comprise bacteria to be detected. Microbial and bacterial growth media are composed of various nutrients to support the growth of the microbial cultures. Such nutrients may include a carbon source, nitrogen source, a source of usable potassium, amino acids, salts, vitamins and their cofactors, metabolic intermediates and minerals.

Carbon sources may include tryptone, peptone, casein and sugars, preferably lactose and glucose.

Nitrogen sources may include amino acids, tryptone, peptone, casein extract, and ammonium sulphate.

Salts may include ferric chloride, copper sulfate, manganese sulfate, potassium chloride, potassium iodide, zinc sulfate, magnesium chloride, potassium phosphate monobasic, potassium phosphate dibasic, sodium carbonate, magnesium sulfate, sodium chloride, calcium chloride and sodium pyruvate.

Vitamins may include biotin, pantothenate, folic acid, inositol, p-aminobenzoic acid, pyridoxine hydrochloride, riboflavin and thiamine.

A common source of amino acids, vitamins and minerals, as well as carbon and nitrogen, is yeast extract, which may form part of the growth medium. Blood may also be used to supplement growth media with necessary nutrients.

Additionally, a microbial growth medium may contain antibacterial or antifungal compounds to aid in selecting and amplifying the microbes of interest.

Detergents may be included to act as dispersing agents, without any antibacterial activity.

To generate a colour, the cleaved diol must chelate an ion, which is derived from a metal compound. The metal compound is preferably an iron compound and most preferably a water soluble iron salt of an organic or inorganic acid, e.g. iron (III) ammonium citrate, iron(II) gluconate, iron(II) acetate, iron(II) citrate, or iron(II) chloride. The iron compound can be iron(II) or iron(III). It will be appreciated by the skilled person that at least trace quantities of iron may be present in media or samples; however, it is usually necessary to supplement the medium with sufficient quantities of an iron compound for the invention to work. The concentration of iron in the growth medium is preferably 0.2 to 1 g/l.

It may be desirable to use the method in conjunction with a substrate capable of detecting another enzyme activity, preferably a nitrophenyl derivative. It is therefore important that the colour resulting from the other test does not interfere with or mask the colour produced by the DHN substrate. It was found that the pale yellow colour of the ONPG substrate does not interfere with visualising the darker colour of the DHN substrate upon cleavage.

The method of the first aspect of the invention is useful for detecting the presence of microbes, for instance microbial contamination of food, drinks, or water that will come into contact with humans or animals. Particularly useful substrates in the method are for detecting glucuronidase or galactosidase which are useful microbial markers. The method may be carried out according to routine test protocols and using standard sampling methods, and growth stages. The results are observed visually or by machine, usually with incident visible light. Incubation may be overnight, but for samples with high levels of enzyme already present shorter incubation may be sufficient, for instance after 1 hour's incubation, sometimes 4-6 hours incubation. Incubation temperatures are selected according to the species being detected and may be at room temperature, but is more often at raised temperature in the range of 30 to 50° C., preferably in the range 35 to 45° C.

Some of the enzyme substrates are new. According to a fourth aspect of the invention there is provided an enzyme substrate of the general formula II

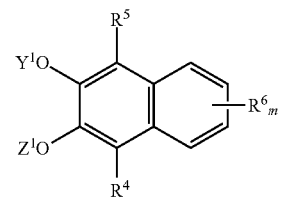

wherein one of the following applies
i) m=0, $R^4=R^5=Z^1=H$, $Y^1$ is selected from the group consisting of D-glucuronyl and D-ribofuranosyl;
ii) m=2, each $R^6$ is Br, $R^4=R^5=H$ or Br, $Z^1=H$, $Y^1$ is glycosyl or phosphate;
iii) m=1, $R^6$ is $-SO_3X$, X is H or $M^+$ wherein $M^+$ is alkali metal ion or a non-metal ion, $Y^1$ is glycosyl and $R^4=R^5=Z^1=H$;
iv) m=0, $R^4=NO_2$, $R^5=Z^1=H$, $Y^1$=glycosyl.

These novel substrates are utilised in compositions with a metal component. The novel compounds are made from DHN or protected or derivatised versions thereof, and hydroxyl-group containing starting materials or acids, using conventional conjugation chemistry with necessary protection/deprotection of functional groups.

DETAILED DESCRIPTION OF EMBODIMENTS OF THE INVENTION

Among the compounds possessing the ortho-dihydroxyaromatic system, DHN and DHN-6-sulfate are well-known metal chelators. They form coloured complexes with a variety of different metals, including first row transition metals such as iron, titanium and vanadium [V. Patrovsky, Coll. Czech. Chem. Commun., 35, 1599-1604, (1970)]. The use of transition metal complexes of DHN, DHN-6-sulfate and some related ortho-dihydroxyaromatic compounds as potential or actual analytical reagents has been reviewed [P. K. Tarafder and R. K. Mondal, Rev. Anal. Chem., 30, 73-81, (2011)]. Until the present invention, DHN and its simple derivatives have not been considered as the core molecule part of chromogenic enzyme substrates. When the DHN substrates of the present invention are incorporated into microbiological growth media containing an iron compound, enzymatic cleavage by microorganisms liberates the free DHN molecule. This reacts spontaneously with the iron compound to generate a highly coloured chelate that allows easy detection of any enzyme-positive reactions by eye (i.e., by the means of incident visible light). The colour given by the reaction depends upon the substitution pattern of the DHN-derivative, and may also be influenced by pH and the mix of oxidation states of the iron, as well as the presence of other components contained in the growth medium. The colour may be described variously as brown, purple or maroon. However, whatever its hue, the colour is completely different to that of most microbiological growth media and is intense enough to allow unambiguous detection of enzyme-positive reactions.

Until the present work, only a very limited number of DHN derivatives having the potential to act as chromogenic enzyme substrates had been made, although DHN itself has been known for over 100 years. It is only much more recently that glycosides of DHN have been synthesised. Ellervik and co-workers described the synthesis of DHN-β-D-xylopyranoside [M. Jacobsson and U. Ellervik, Tetrahedron Letters, 43, 6549-6552, (2002)] and DHN-di-β-D-xylopyranoside [R. Johnsson et al, Bioorganic and Medicinal Chemistry, 15, 2868-2877, (2007)] as part of a large set of other compounds to investigate their antiproliferative effects on cancer cells. Sakuma and Yokoe described the preparation of DHN-β-D-glucopyranoside (4) [K. Sakuma and I. Yokoe, Japanese Patent Publication No. 2004-224763, (2004)]. This compound was advocated as a potential bleaching agent for use in cosmetics [K. Sakuma and I. Yokoe, Japanese Patent Publication No. 2004-224762, (2004)]. Clearly, none of the aforementioned prior art concerning DHN compounds is pertinent to the present application wherein they are employed as chromogenic enzyme substrates for the detection of microorganisms. Nor is the more recent technique of Bhowmik and Maitra [(S. Bhowmik and U. Maitra, Chem. Commun., 48, 4624-4626, (2012)] wherein these authors described the development of a time-delayed luminescence method for detecting enzyme activity using terbium(III) acetate in conjunction with either DHN-β-D-glucopyranoside (4) or DHN-diesters. This method differs greatly from the present invention in several important respects. Firstly, it is a luminescence method in which the luminescence is triggered by excitation of the sample with ultraviolet light, whereas the present invention is a chromogenic method involving absorbance of light in the visible spectrum. Bhowmik and Maitra reported that their technique (which they state does not involve chelation) works exclusively in a gel medium, and this is a further major difference from the present invention which works very well in a fluid or liquid medium as well as in agar gels. A third important difference is that the necessary gelling agent of Bhowmik and Maitra was the sodium salt of a bile acid, cholic acid. Cholic acid and other bile acids have long been known to inhibit the growth of certain microorganisms [Binder et al, Amer. J. Clin. Nutr., 28, 119-125, (1975); Kurdi et al, J. Bacteriol., 188, 1979-1986, (2006)]. The concentration of sodium cholate used by Bhowmik and Maitra was 15 mM, and there was no suggestion by these authors that microorganisms are able to grow in or on their reaction medium. In this context it should be noted that the growth of some intestinal bacteria is completely suppressed with cholic acid concentrations lower than 15 mM [Floch et al, Amer. J. Clin. Nutr., 25, 1418-1426, (1972)]. Additionally, it should be remarked that the present invention requires the incorporation of metal compounds, e.g. first transition metal series metal compounds, preferentially iron compounds, into the medium. The iron compounds may be either iron(II) or iron(III); or a mixture of both states. In some instances, if other metal ions are substituted for iron, including ions such as Ti(IV) that are known to form coloured complexes with DHN, then little or no visible colour is developed after enzymatic hydrolysis. Similarly, using the lanthanide terbium(III) acetate instead of an iron compound does not furnish a coloured end-product. The metal compound used in the invention must therefore be selected having regard to the colour-forming capability with the cleaved product of the enzymatic reaction.

Substitution products of the DHN core molecule yield both enzyme substrates and endpoints of very different solubilities, and this is a further useful feature of the present invention. Thus, unsubstituted-DHN compounds are fairly water-soluble and the soluble DHN-iron chelate is best suited to liquid growth media. Compounds derived from DHN-6-sulfate are even more water soluble and may be preferred when the solubility of the enzyme substrates in aqueous media is problematic, for instance in the development of assays for esterases such as lipase which require substrates that are derivatives of fatty acids and may have limited water solubility unless derivatised by ionic groups elsewhere in the molecule. In contrast, substrates based on 6,7-dibromo-DHN (as described below) give insoluble precipitates with iron compounds and they are particularly suited to agar plate media, where they are able to visualise single colonies.

Preferred and non-limiting aspects of the invention are described in more detail below, which includes worked examples of microbial test methods using chromogenic substrates, followed by synthetic methods used to make the substrates.

Example 1—Testing of DHN-β-D-Galactopyranoside with a Variety of Microorganisms

DHN is inexpensive and readily available commercially. We found that novel glycosides of it could be prepared by standard means. Thus the protected DHN-β-D-galactopyranoside (7) was made by coupling acetobromogalactose with DHN in acetone-water in the presence of sodium hydroxide. After work-up, deprotection in methanol containing a catalytic quantity of sodium methoxide furnished the desired DHN-β-D-galactopyranoside (8) as an off-white solid. Details of the synthesis are given below in syntheses 7 and 8.

This compound was tested on agar plates by multi-point inoculation. The plates were made from Columbia agar (Oxoid, Basingstoke, UK) (100 ml) supplemented with ferric ammonium citrate (FAC) (50 mg). After the agar had been autoclaved (121° C.) and cooled to 50° C., a filter sterilized solution of the substrate (8) (30 mg) dissolved in N-methylpyrrolidone (NMP) (200 μL) was added, thus giving a substrate concentration of 300 mg/L. After pouring, the plates were inoculated with a range of microorganisms and incubated at 37° C. for 18 h in air (Table 1). Those organisms positive for β-galactosidase could be easily distinguished from those negative for this enzyme by the development of a strong purple-maroon colour in the former.

TABLE 1

| Organism | DHN-β-D-galactopyranoside 8 Colour |
|---|---|
| 1 *Escherichia coli* NCTC 10418 | ++ |
| 2 *Klebsiella pneumoniae* NCTC 9528 | ++ |
| 3 *Providencia rettgeri* NCTC 7475 | − |
| 4 *Enterobacter cloacae* NCTC 11936 | ++ |
| 5 *Serratia marcescens* NCTC 10211 | + |
| 6 *Salmonella typhimurium* NCTC 74 | − |
| 7 *Pseudomonas aeruginosa* NCTC 10662 | − |
| 8 *Yersinia enterocolitica* NCTC 11176 | − |
| 9 *Burkholderia cepacia* NCTC 10931 | − |
| 10 *Acinetobacter baumannii* NCTC 19606 | − |
| 11 *Steptococcus pyogenes* NCTC 8306 | − |
| 12 *Staphylococcus aureus* (MRSA) NCTC 11939 | − |

TABLE 1-continued

| Organism | DHN-β-D-galactopyranoside 8 Colour |
|---|---|
| 13 Staphylococcus aureus NCTC 6571 | – |
| 14 Staphylococcus epidermidis NCTC 11047 | – |
| 15 Listeria monocytogenes NCTC 11994 | – |
| 16 Enterococcus faecium NCTC 7171 | Tr. |
| 17 Enterococcus faecalis NCTC 775 | – |
| 18 Bacillus subtilis NCTC 9372 | – |
| 19 Candida albicans ATCC 90028 | – |
| 20 Candida glabrata NCPF 3943 | – |

Unless indicated otherwise, the symbols in each table have the following meaning: ++ means strong colour; + means less colour than ++; +/− means less colour than +; Tr means a trace of colour, less than +/−; − means no colour. The substrate (8) showed no obvious toxicity with any of the Gram-positive or Gram-negative strains tested. Essentially identical results were obtained if other iron salts (e.g. iron(II) gluconate, iron(II) acetate, iron(II) citrate, iron(II) acetylacetonate, and iron(III) acetylacetonate) were substituted in place of FAC. The iron compound can be either iron(II) (i.e. ferrous) or iron(III) (i.e. ferric). Both types of compound work well. The coloured chelate was still formed when the plates were incubated under anaerobic conditions, which is another useful feature of the present invention, it will be appreciated that the media and the reagents will all contain at least traces of iron compounds. However, the invention does not work unless the medium is supplemented with a sufficient amount of an iron compound. Concentrations of 200-600 mg/L of iron compound were found to be satisfactory. In contrast, supplementing the growth media with compounds of other metals gives either no coloured endpoint or an extremely poor one to visualise. In an alternative to the above procedure, the substrate may be added to the agar prior to being autoclaved (121° C. for 20 minutes) with no decrease in sensitivity. The colour generated by DHN in combination with an iron salt is of about the same intensity as that previously demonstrated by the reaction between 1,2-dihydroxybenzene (catechol) and an iron salt at the same concentration [M. Burton, EP1438423, (2007)]. However, the colours are different (the catechol-iron complex is black in solution) and this may be an advantage in designing a particular test medium. DHN-β-D-galactopyranoside (8) may find application as an alternative to the widely used enzyme substrate ONPG.

Example 2—Other DHN Substrates and Cleavage by Microorganisms with a Range of Enzymatic Marker Activities Several other DHN substrates, intended for some of the most frequently encountered hydrolase activities in diagnostic microbiology, were synthesised by the methods described below. These were the glycosides β-D-glucopyranoside (4), α-D-glucopyranoside (6), α-D-galactopyranoside (10) and N-acetyl-β-D-glucosaminide (15), the esterase substrate DHN-dicaprylate (16) and the phosphatase substrate, DHN-phosphate disodium salt (17). DHN-β-D-ribofuranoside (2) was also made. When evaluated in the same manner as DHN-β-D-galactopyranoside (8), in general these substrates were hydrolysed according to the known enzyme profiles of the test strains (Tables 2 and 3). However, DHN-β-D-ribofuranoside (2) (Table 2) was of particular interest.

TABLE 2

| Organism | DHN-β-D-ribofuranoside 2 Colour | DHN-α-D-galactopyranoside 10 Colour | DHN-α-D-glucopyranoside 6 Colour | DHN-N-acetyl-β-D-glucosaminide 15 Colour |
|---|---|---|---|---|
| 1 Escherichia coli NCTC 10418 | ++ | Tr. | + | – |
| 2 Serratia marcescens NCTC 10211 | ++ | – | ++ | ++ |
| 3 Pseudomonas aeruginosa NCTC 10662 | – | – | – | – |
| 4 Burkholderia cepacia 1222 | – | – | – | – |
| 5 Yersinia enterocolitica NCTC 11176 | – | – | Tr. | + |
| 6 Salmonella typhimurium NCTC 74 | ++ | – | – | – |
| 7 Citrobacter freundii NCTC 9750 or 46262 | ++ | – | – | – |
| 8 Morganella morganii 462403 (wild) | ++ | – | – | – |
| 9 Enterobacter cloacae NCTC 11936 | ++ | Tr. | ++ | +/− |
| 10 Providencia rettgeri NCTC 7475 | ++ | – | – | – |
| 11 Bacillus subtilis NCTC 9372 | – | – | ++ | – |
| 12 Enterococcus faecails NCTC 775 | – | – | ++ | ++ |
| 13 Enterococcus faecium NCTC 7171 | – | – | Tr. | ++ |
| 14 Staphylococcus epidermidis NCTC 11047 | – | – | + | – |
| 15 Staphylococcus aureus NCTC 6571 | + | – | +/− | – |
| 16 MRSA NCTC 11939 | + | – | +/− | – |
| 17 Steptococcus pyogenes NCTC 8306 | – | – | ++ | ++ |
| 18 Listeria monocytogenes NCTC 11994 | – | – | ++ | ++ |
| 19 Candida albicans ATCC 90028 | – | – | – | – |
| 20 Candida glabrata NCPF 3943 | – | – | – | – |

TABLE 3

| Organism | DHN-dicaprylate 16 Colour | DHN-β-D-glucopyranoside 4 Colour | DHN-phosphate disodium salt 17 Colour |
|---|---|---|---|
| 1 Escherichia coli NCTC 10418 | – | Tr. | +/− |
| 2 Klebsiella pneumoniae NCTC 9528 | – | ++ | ++ |
| 3 Providencia rettgeri NCTC 7475 | + | ++ | + |
| 4 Enterobacter cloacae NCTC 11936 | – | + | +/− |
| 5 Serratia marcescens NCTC 10211 | + | ++ | ++ |

TABLE 3-continued

| Organism | DHN-dicaprylate 16 Colour | DHN-β-D-glucopyranoside 4 Colour | DHN-phosphate disodium salt 17 Colour |
|---|---|---|---|
| 6 *Salmonella typhimurium* NCTC 74 | − | − | ++ |
| 7 *Pseudomonas aeruginosa* NCTC 10662 | + | − | − |
| 8 *Yersinia enterocolitica* NCTC 11176 | − | − | +/− |
| 9 *Burkholderia cepacia* NCTC 10931 | − | − | +/− |
| 10 *Acinetobacter baumannii* NCTC 19606 | + | − | − |
| 11 *Steptococcus pyogenes* NCTC 8306 | − | − | − |
| 12 *Staphylococcus aureus* (MRSA) NCTC 11939 | − | − | + |
| 13 *Staphylococcus aureus* NCTC 6571 | − | − | + |
| 14 *Staphylococcus epidermidis* NCTC 11047 | − | − | − |
| 15 *Listeria monocytogenes* NCTC 11994 | − | + | + |
| 16 *Enterococcus faecium* NCTC 7171 | − | + | − |
| 17 *Enterococcus faecalis* NCTC 775 | − | + | − |
| 18 *Bacillus subtilis* NCTC 9372 | − | + | − |
| 19 *Candida albicans* ATCC 90028 | − | − | − |
| 20 *Candida glabrata* NCPF 3943 | − | − | − |

When challenged with three strains of staphylococci, only the *S. aureus* strains NCTC 6571 and MRSA NCTC 11939 were able to hydrolyse it. It was unaffected by *S. epidermidis* NCTC 11047. This strongly suggests that DHN-β-D-ribofuranoside (2) has potential utility in the detection of MRSA and is able to differentiate this organism from other species of staphylococci that can cause interference in its positive identification. Other chromogenic β-D-ribofuranosides have already been evaluated for this purpose [M. Burton, EP1438424, (2006)]. The unsubstituted DHN-glycosides tested in the present invention were all prepared by means that have been reported in the literature for other mono- or di-phenolic aglycones. The various glycosyl donors employed were all readily prepared intermediates such as acetohalosugars or trichloroacetimidates. One disadvantage of DHN enzyme substrates in agar plate media is that the coloured iron-complex diffuses, as occurs also with substrates made from 1,2-diydroxybenzene or esculetin. The diffusion is no greater than that which occurs with esculin (the β-D-glucopyranoside of esculetin). As esculin is used commercially in agar plate media, substrates derived from DHN may also find application in agar plate media notwithstanding their capacity to diffuse. However, it would seem that they are much more advantageously employed in liquid broth media or in agar tube media.

Example 3—DHN-β-D-Glucuronide Substrates and their Testing on Various Microorganisms Tube or liquid media containing the fluorogenic compound MUG (4-methylumbelliferyl β-D-glucuronide) are extensively used to detect *E. coli*. Often these systems also contain the substrate ONPG for the detection of β-D-galactosidase activity and therefore total coliforms. The media Colitag® (CPI international, Santa Rosa, USA) and ColiLert® (Idexx Laboratories, Westbrook, USA) both utilise MUG plus ONPG for detecting *E. coli* and total coliforms. The disadvantage of MUG is that a UV source is required to visualise the fluorescence associated with *E. coli*. It would be an advantage to have a chromogenic glucuronide that can detect *E. coli* with incident visible light. Accordingly, the novel compound DHN-β-D-glucuronide (12) was prepared in both its cyclohexylammonium salt form (12a) (hereinafter referred to as the CHA salt) and its sodium salt form (12b). In the preliminary evaluation against twenty different microorganisms on agar plates containing FAC, both salt forms of the DHN-β-D-glucuronide (12a and 12b) were hydrolysed equally well by *E. coli* (as judged by the strong colour produced with each) (Table 4). Just as significantly, *E. coli* was the only species able to effect hydrolysis; the other 19 strains were all β-D-glucuronidase negative.

TABLE 4

| Organism | DHN-β-D-glucuronide CHA salt 12a Colour | DHN-β-D-glucuronide sodium salt 12b Colour |
|---|---|---|
| 1 *Escherichia coli* NCTC 10418 | ++ | ++ |
| 2 *Serratia marcescens* NCTC 10211 | − | − |
| 3 *Pseudomonas aeruginosa* NCTC 10662 | − | − |
| 4 *Burkholderia cepacia* 1222 | − | − |
| 5 *Yersinia enterocolitica* NCTC 11176 | − | − |
| 6 *Salmonella typhimurium* NCTC 74 | − | − |
| 7 *Citrobacter freundii* NCTC 9750 or 46262 | − | − |
| 8 *Morganella morganii* 462403 (wild) | − | − |
| 9 *Enterobacter cloacae* NCTC 11936 | − | − |
| 10 *Providencia rettgeri* NCTC 7475 | − | − |
| 11 *Bacillus subtilis* NCTC 9372 | − | − |
| 12 *Enterococcus faecails* NCTC 775 | − | − |
| 13 *Enterococcus faecium* NCTC 7171 | − | − |
| 14 *Staphylococcus epidermidis* NCTC 11047 | − | − |
| 15 *Staphylococcus aureus* NCTC 6571 | − | − |
| 16 MRSA NCTC 11939 | − | − |
| 17 *Steptococcus pyogenes* NCTC 8306 | − | − |
| 18 *Listeria monocytogenes* NCTC 11994 | − | − |
| 19 *Candida albicans* ATCC 90028 | − | − |
| 20 *Candida glabrata* NCPF 3943 | − | − |

Example 4—Sensitivity of DHN-β-D-Glucuronide to Various *E. coli* Isolates Compared to Standard Chromogenic Indoxyl Glucuronide Substrates In order to obtain a fuller picture of the sensitivity of DHN-β-D-glucuronide (12a) it was screened with 100 different clinical isolates of *E. coli* in a liquid medium containing FAC. The isolates were chosen at random from the Microbiology Department, Freeman Hospital, Newcastle Upon Tyne, UK. The effectiveness of DHN-β-D-glucuronide (12a) was compared with three other media which all contained indoxyl-β-D-glucuronides. One was a commercial medium, CPS ID 3 (bioMèrieux SA, Lyon, France). CPS ID 3 contains complementary chromogenic substrates; Rose-β-D-glucuronide (6-chloro-3-indolyl β-D-glucuronide) of undisclosed salt form [at 250 mg/L] for the detection of β-D-glucuronidase activity (producing red or pink colonies) and X-β-D-glucoside (5-bromo-4-chloro-3-indoyl β-D-glucopyranoside) [50 mg/L] for the detection of β-D-glucosidase (producing green colonies) [M. Casse et al, U.S. Pat. No. 8,216,802 (2012)]. This medium was employed as a control. Among the β-D-glucuronidase producing strains of E. coli there is a large variation in the quantity of the enzyme produced and it is almost certain that the CPS ID 3 media has been rigorously optimised to allow good growth of all the target organisms and maximum expression of the target enzymes. Therefore, two indoxyl glucuronides, X-β-D-glucuronide CHA salt and Rose-β-D-glucuronide CHA salt were also tested in a simple agar medium to allow a direct comparison of the sensitivity of these indoxyl glucuronides when used in a medium that has not been optimised for the growth of the target organism. The comparison of the results for Rose-β-glucuronide and the CPS ID 3 medium was of particular significance as the commercial medium also uses Rose-β-glucuronide for the detection of E. coli For consistency, the three glucuronides were all chosen as their CHA salts. As already stated, is not anticipated that the salt form is critical to their performance. Currently, X-β-D-glucuronide is often used as either the CHA salt or the sodium salt. Brenner and colleagues [K. P. Brenner et al, Appl. Environ. Microbiol., 59, 3534-3544, (1993)] found no difference in the performance of the CHA and sodium salt forms with their application using indoxyl-β-D-glucuronide, neither in respect of colour development nor in the recovery of E. coli.

The two indoxyl glucuronides used produce insoluble endpoints following hydrolysis, as does the CPS ID 3 medium. It was therefore necessary to test these two substrates on agar plates. In contrast, DHN-β-D-glucuronide (12) gives a much more soluble endpoint best suited to liquid media and was therefore tested in a broth medium. The broth was prepared using proteose peptone (2 g), NaCl (1 g) and FAC (100 mg) in DI water (180 mL). This mixture was autoclaved and cooled to room temperature before being dispensed into bijoux (100×1.8 mL). DHN-β-D-glucuronide CHA salt (12a) (60 mg) was dissolved in water (20 mL) and filtered to sterilize before being aseptically dispensed into successive bijoux (0.2 mL) containing the broth solution. The broth/substrate solutions were then inoculated with bacterial suspensions made up to 0.5 McFarland standard (2 μL per bijoux). X-β-D-glucuronide CHA salt (Glycosynth Ltd, Warrington, UK) (10 mg) was dissolved in NMP (200 μL). Rose-f-D-glucuronide CHA salt (Glycosynth Ltd, Warrington, UK) (20 mg) was dissolved in NMP (200 μL). These solutions were then added to Columbia agar (Oxoid, Basingstoke, UK) (100 mL) and inoculated with bacterial suspensions made up to 0.5 McFarland standard (1 μL). The strains of E. coli used are listed in table 5. The plates and broths were incubated at 37° C. for 18 hours in air. The green colonies seen on the CPS ID 3 media were indicative of β-D-glucosidase activity.

TABLE 5

| Ref | Organism | Reference | CPS ID 3 agar | X-β-D-glucuronide CHA salt | Rose-β-D-glucuronide CHA salt | DHN-β-D-glucuronide CHA salt 12a broth |
|---|---|---|---|---|---|---|
| 1 | E. coli | 260471B | +/−Red | − | − | − |
| 2 | E. coli | 260464G | Red | Green | Red | Purple |
| 3 | E. coli | 260481J | Red | Green | Red | Purple |
| 4 | E. coli | 260480M | Red | Green | Red | Purple |
| 5 | E. coli | 260521S | Red | Green | Red | Purple |
| 6 | E. coli | 260578D | +/−Red | − | − | − |
| 7 | E. coli | 260537E | Red | − | − | − |
| 8 | E. coli | 260522Z | Red | Green | Red | Purple |
| 9 | E. coli | 260541R | +/−Red | Green | Red | Purple |
| 10 | E. coli | 260538H | Red | − | − | − |
| 11 | E. coli | 260539Y | Red | Green | Red | Purple |
| 12 | E. coli | 260545G | Red | Green | Red | Purple |
| 13 | E. coli | 260459W | Red | Green | Red | Purple |
| 14 | E. coli | 260458Y | Red | Green | Red | Purple |
| 15 | E. coli | 260441G | Red | Green | Red | Purple |
| 16 | E. coli | 260440S | Red | Green | Red | Purple |
| 17 | E. coli | 260508Y | Red | Green | Red | Purple |
| 18 | E. coli | 260504N | Red | Green | Red | Purple |
| 19 | E. coli | 260503Z | Red | Green | Red | Purple |
| 20 | E. coli | 260554D | Red | Green | Red | Purple |
| 21 | E. coli | 260502G | Red | Green | Red | Purple |
| 22 | E. coli | 260532S | Red | Green | Red | Purple |
| 23 | E. coli | 260533G | Red | Green | Red | Purple |
| 24 | E. coli | 260536Q | Red | Green | Red | Purple |
| 25 | E. coli | 260548Q | Red | Green | Red | Purple |
| 26 | E. coli | 260549E | Red | Green | Red | Purple |
| 27 | E. coli | 260553X | − | − | − | − |
| 28 | E. coli | 260547N | Red | Green | Red | Purple |
| 29 | E. coli | 260563B | Red | Green | Red | Purple |
| 30 | E. coli | 260564R | Red | Green | Red | Purple |
| 31 | E. coli | 260555L | Red | Green | Red | Purple |
| 32 | E. coli | 260511X | Red | Green | Red | Purple |
| 33 | E. coli | 260515Z | Red | − | Red | Purple |
| 34 | E. coli | 260514G | Red | − | − | − |
| 35 | E. coli | 260505Q | Red | − | − | − |
| 36 | E. coli | 260510R | Red | Green | Red | Purple |
| 37 | E. coli | 260364H | Tr. Red | − | − | − |
| 38 | E. coli | 260406Y | Red | Green | Red | Purple |
| 39 | E. coli | 260492J | Red | Green | Red | Purple |
| 40 | E. coli | 260486L | Red | Green | Red | Purple |
| 41 | E. coli | 260485D | Red | Green | Red | Purple |
| 42 | E. coli | 260479Q | Red | Green | Red | Purple |
| 42 | E. coli | 260506E | Red | Green | Red | Purple |
| 44 | E. coli | 260478N | Tr. Red | − | − | − |
| 45 | E. coli | 260463D | Red | Green | Red | Purple |
| 46 | E. coli | 260396Z | Red | Green | Red | Purple |
| 47 | E. coli | 260370C | Red | Green | Red | Purple |
| 48 | E. coli | 260262P | Red | Green | Red | Purple |
| 49 | E. coli | 260280Z | Red | Green | Red | Purple |
| 50 | E. coli | 260375E | Red | Green | Red | Purple |

| Ref | Organism | Reference | CPS3 agar | X-β-D-glucuronide CHA salt | Rose-β-D-glucuronide CHA salt | DHN-β-D-glucuronide CHA salt 12a broth |
|---|---|---|---|---|---|---|
| 51 | E. coli | 260400N | − | − | − | − |
| 52 | E. coli | 260404W | Red | Green | Red | Purple |
| 53 | E. coli | 260401Q | Red | Green | Red | Purple |
| 54 | E. coli | 260402H | Red | Green | Red | Purple |
| 55 | E. coli | 260411Z | Red | Green | Red | Purple |
| 56 | E. coli | 260407F | Red | Green | Red | Purple |
| 57 | E. coli | 260408C | Red | Green | Red | Purple |
| 58 | E. coli | 260509W | Red | Green | Red | Purple |
| 59 | E. coli | 260433H | Red | Green | Red | Purple |
| 60 | E. coli | 260432E | Red | Green | Red | Purple |
| 61 | E. coli | 260431N | Red | Green | Red | Purple |
| 62 | E. coli | 260428T | Red | Green | Red | Purple |
| 63 | E. coli | 260426F | Red | Green | Red | Purple |
| 64 | E. coli | 260425A | Red | Green | Red | Purple |
| 65 | E. coli | 260483R | − | − | − | − |

TABLE 5-continued

| | | | | | | |
|---|---|---|---|---|---|---|
| 66 | E. coli | 260494B | Red | Green | Red | Purple |
| 67 | E. coli | 260495R | – | – | – | Purple |
| 68 | E. coli | 260439C | Red | Green | Red | Purple |
| 69 | E. coli | 260438F | Red | Green | Red | Purple |
| 70 | E. coli | 260437A | Red | – | Tr. Red | – |
| 71 | E. coli | 260412Q | Red | Green | Red | Purple |
| 72 | E. coli | 260497D | Red | Green | Red | Purple |
| 73 | E. coli | 260416W | Red | – | – | Purple |
| 74 | E. coli | 260417P | Red | Green | Red | Purple |
| 75 | E. coli | 260422Y | Red | Green | Red | Purple |
| 76 | E. coli | 260406A | Red | – | – | – |
| 77 | E. coli | 260405P | Red | Green | Red | Purple |
| 78 | E. coli | 260399E | Red | Green | Red | Purple |
| 79 | E. coli | 260435W | Red | Green | Red | Purple |
| 80 | E. coli | 260434Y | Red | Green | Red | Purple |
| 81 | E. coli | 2603121P | Tr. Red | – | – | – |
| 82 | E. coli | 260310H | Red | Green | Red | Purple |
| 83 | E. coli | 260436P | Red | Green | Red | Purple |
| 84 | E. coli | 260398Q | Red | Green | Red | Purple |
| 85 | E. coli | 260345F | Red | Green | Red | Purple |
| 86 | E. coli | 260390B | – | – | – | – |
| 87 | E. coli | 260414H | Red | Green | Red | Purple |
| 88 | E. coli | 260415Y | Red | Green | Red | Purple |
| 89 | E. coli | 260313A | Tr. Red | – | – | – |
| 90 | E. coli | 260316T | – | – | – | – |
| 91 | E. coli | 260424P | Red | Green | Red | Purple |
| 92 | E. coli | 260348K | Red | Green | Red | Purple |
| 97 | E. coli | 260354W | Red | Green | Red | Purple |
| 98 | E. coli | 260333P | – | – | – | – |
| 99 | E. coli | 260330Y | Red | Green | Red | Purple |
| 100 | E. coli | 260327V | Red | Green | Red | Purple |
| 101 | E. cloacae | 260329R | Tr. Green | – | – | – |
| 102 | E. cloacae | NCTC 11936 | Tr. Green | – | – | – |
| 103 | E. faecium | NCTC 7171 | Green | – | – | – |
| 104 | E. faecalis | NCTC 775 | Green | – | – | – |
| 105 | E. coli | O157 non-toxigenic | – | – | – | – |

Red, Green, Black or Purple mean strong colour; +/−means less colour than strong; Tr means a trace of colour, less than +/−; − means no colour.

The results of table 5 (lines 1-100) are summarised below (Table 6) for the 100 E. coli strains after 18 h incubation:

TABLE 6

| Substrate/Medium | Negative strains | Positive strains | % Sensitivity |
|---|---|---|---|
| CPS ID 3 | 7 | 93 | 93 |
| DHN-β-D-glucuronide CHA salt 12a broth | 18 | 82 | 82 |
| Rose-β-D-glucuronide CHA salt | 19 | 81 | 81 |
| X β-D-glucuronide CHA salt | 21 | 79 | 79 |

The commercial medium, CPS ID3, was the most sensitive with 93100 of E. coli strains giving red colonies. The excellent performance of this medium was to be expected, as it most probably contains inducers of 0-D-glucuronidase activity and/or optimal conditions for the expression of this enzyme. That not all strains were detected by this medium is understandable, as a small percentage of all E. coli strains is negative for β-D-glucuronidase. Surprisingly, the next most sensitive medium was DHN-β-D-glucuronide (12a) [purple solutions] 82/100 strains. The novel substrate showed higher sensitivity than Rose-β-D-glucuronide [red colonies] (81/100 strains) when it was used in the simple Columbia agar medium. Considering that Rose-β-D-glucuronide is the same substrate as employed in the CPS ID3 medium, it shows how those skilled in the art can develop a medium to increase the sensitivity of the substrate when challenged with many different strains of microorganisms.

X-β-D-glucuronide [green colonies] gave the lowest sensitivity (79/100 strains) in the simple agar medium, yet this substrate is currently very extensively used in commercial media to detect E. coli. More surprising still, DHN-β-D-glucuronide (12a) visualised one strain (E. coli 260495R) that was not detected by CPS ID3 or by the other two media containing the indoxyl glucuronides. In addition to the 100 strains of E. coli, all four media were tested with four other stains of Enterobacteriaceae known to be 1-D-glucuronidase-negative, as well as one β-D-glucuronidase-negative strain of E. coli (E. coli 0157 non-toxigenic) (Table 5, lines 101-105). All five of these strains were negative on all the media, thus showing 100% specificity for β-D-glucuronidase-producing E. coli over these other organisms.

Example 5—Combination of DNH-β-D-Glucuronide and ONPG to Simulate a Dual Chromogenic Systems for Distinguishing Galactosidase and Glucuronidase Positive/Negative Microorganisms Because many E. coli produce both β-D-glucuronidase and β-D-galactosidase, DHN-β-D-glucuronide (12a) was tested as in the broth medium described above but in the presence of ONPG (at a concentration of 1.5 g/L). This was done to see if the colour produced by the iron complex could mask the yellow of o-nitrophenol. This would be essential to successfully visualise any E. coli in a dual-chromogenic (or possibly multi-chromogenic) system. It was found that E. coli expressing both β-D-glucuronidase and β-D-galactosidase now gave purple-brown solutions with DHN-β-D-glucuronide (12a). The colour of these solutions of mixed chromogens could be very readily distinguished with the unaided eye from the yellow colour of those strains, such as E. cloacae, that produced β-D-galactosidase only. Similarly, a combination of DHN-β-D-glucuronide (12a) with ONPG was able to detect the β-D-glucuronidase activity of Shigella sonnei, an important pathogen that is generally positive for both β-D-glucuronidase and β-D-galactosidase. The above results clearly demonstrate the potential of DHN-β-D-glucuronide (12) to be used in a liquid medium to detect E. coli, either on its own or in combination with other substrates (e.g. with ONPG). Although the strains tested were of clinical origin, it will be appreciated that DHN-4-D-glucuronide (12) of the present invention may be used to screen samples from food, environmental sources and water. Moreover, those skilled in the art of developing such media could add other ingredients, such as specific enzyme or growth inducers, enzyme or growth inhibitors or other metabolic regulators to ensure the optimum performance of the substrates within the media. Inducers of β-D-glucuronidase in an enzymatic method for detecting E. coli have been disclosed [H. Nelis, U.S. Pat. No. 5,861,270, (1999)] and a commercially produced enzyme inducer cocktail has been used in a test for the enumeration of E. coli in drinking water [S. O. Van Poucke and H. J. Nelis, J. Appl. Microbiol., 89, 390-396, (2000)]. In the method of Monget et al for identifying E. coli from biological samples [D. Monget et al, U.S. Pat. No. 8,334,112 (2012)] glucuronate and methyl-β-glucuronide are cited as the preferred inducers of β-glucuronidase. DHN-β-D-glucuronide-6-methyl ester (13) was also hydrolysed by β-D-glucuronidase-positive strains, but the colour was weaker than with (12a) or (12b).

Example 6—Nitrated DHN-Substrate

Having established the utility of DHN as a useful core molecule as a base for chromogenic enzyme substrates, we sought to address the issue of diffusion of the core molecule that would limit its application in or on solid plate media, such as agar media. A possible way to reduce the solubility of a core molecule is to increase its molecular weight or size. Nitration of the fully protected DHN-β-D-ribofuranoside (1) introduced a nitro group at the 1-position of the DHN nucleus. The method is described in detail below. Deprotection afforded 1-nitro-DHN-β-D-ribofuranoside (19), and this was tested on agar plates with FAC in exactly the same manner as the unsubstituted compound (2). Unfortunately, the 1-nitro-DHN-iron complex still diffused extensively. However, the colour of this chelate was more distinctly red than the DHN-iron complex, so compounds of this type may be preferred over the unsubstituted-DHN derivatives depending on the requirements.

Example 7—Halogenated DHN-Substrates

Halogenation of DHN was then explored. Bromination of DHN was carried out by the method of Zincke and Fries [T. Zincke and K. Fries, Annalen, 334, 365, (1904)]. Using a ratio of 4 mol of molecular bromine to 1 mol of DHN in acetic acid as described by these authors and as detailed below gave the anticipated 1,4-dibromo-DHN in good yield. By increasing the amount of bromine to 8 mol, (again as described by Zincke and Fries), the expected 1,4,6,7-tetrabromo-DHN (20) was also obtained in good yield. Both these brominated derivatives were glycosylated as the β-D-ribofuranosides, after which the substrates were separately incorporated into agar plates containing FAC for microbiological evaluation using a range of organisms previously tried with the unsubstituted DHN-glycosides. The results with both 1,4-dibromo-DHN-β-D-ribofuranoside and 1,4,6, 7-tetrabromo-DHN-β-D-ribofuranoside were equally disappointing; both gave a very strong background colouration to the whole plate making it impractical to see any positive reactions.

In the publication of Zincke and Fries, the authors reported that treatment of 1,4,6,7-tetrabromo-DHN (20) with tin (II) chloride led to the removal of the bromines in the 1 and 4 positions. Their work was repeated and the expected 6,7-dibromo-DHN (21) was obtained smoothly and in good yield (68%). 6,7-Dibromo-DHN (21) is isomeric with the 1,4-dibromo compound which had proven unsuccessful as an aglycone for the detection of microorganisms. Notwithstanding this latter fact, we proceeded to evaluate the properties of 6,7-dibromo-DHN (17) as an aglycone for artificial chromogenic enzyme substrates. Firstly we found that this molecule was efficiently converted into 6,7-dibromo-DHN-β-D-ribofuranoside (23). 6,7-Dibromo-DHN-β-D-ribofuranoside (23) was incorporated into Columbia agar plates containing FAC (500 mg/L) at a substrate concentration of 300 mg/L. The plates were made as described for DHN β-D-galactopyranoside (8), except that the substrate was dissolved in DMSO (200 μL). After inoculation and incubation for 18 h at 37° C. in air, 6,7-dibromo-DHN-β-D-ribofuranoside (23) produced largely discrete red-brown or maroon colonies upon hydrolysis by a number of different Gram-negative bacteria (Table 7). There was little or no diffusion of the colour into the surrounding medium and the background colouration of the plates was minimal. The growth of Gram-positive bacteria was mainly suppressed by this substrate.

TABLE 7

| | Strains A | 6,7-Dibromo-DHN-β-D-ribofuranoside 23 Colour | 6,7-Dibromo-DHN-β-D-galactopyranoside 25 Colour | 6,7-Dibromo-DHN-β-D-galactopyranoside 27 Colour | 6,7-Dibromo-DHN-β-D-glucuronide CHA salt 29 Colour |
|---|---|---|---|---|---|
| 1 | *Escherichia coli* NCTC 10418 | − | ++ | Tr. | ++ |
| 2 | *Serratia marcescens* NCTC 10211 | ++ | + | ++ | − |
| 3 | *Pseudomonas aeruginosa* NCTC 10662 | + | − | − | − |
| 4 | *Burkholderia cepacia* 1222 | +/− | +/− | + | − |
| 5 | *Yersinia enterocolitica* NCTC 11176 | − | − | − | − |
| 6 | *Salmonella typhimurium* NCTC 74 | ++ | − | − | − |
| 7 | *Citrobacter freundii* NCTC 9750 or 46262 | ++ | + | + | − |
| 8 | *Morganella morganii* 462403 (wild) | ++ | − | − | − |
| 9 | *Enterobacter cloacae* NCTC 11936 | ++ | − | − | − |
| 10 | *Providencia rettgeri* NCTC 7475 | − | − | ++ | − |
| 11 | *Bacillus subtilis* NCTC 9372 | − | − | + | − |
| 12 | *Enterococcus faecails* NCTC 775 | − | Tr. | Tr. | − |
| 13 | *Enterococcus faecium* NCTC 7171 | − | +/− | +/− | − |
| 14 | *Staphylococcus epidermidis* NCTC 11047 | − | − | − | − |
| 15 | *Staphylococcus aureus* NCTC 6571 | − | − | Tr. | − |
| 16 | MRSA NCTC 11939 | − | − | Tr. | − |
| 17 | *Steptococcus pyogenes* NCTC 8306 | − | − | − | − |
| 18 | *Listeria monocytogenes* NCTC 11994 | − | +/− | +/− | − |
| 19 | *Candida albicans* ATCC 90028 | − | − | − | − |
| 20 | *Candida glabrata* NCPF 3943 | − | − | − | − |

Example 8—Further Halogenated DHN-Glycosides

Additional glycosides based on 6,7-dibromo-DHN were also produced to show the generality of this aspect of the invention (Table 7). The synthetic methods are described in detail in the section below. The β-D-galactopyranoside (25), the β-D-glucopyranoside (27) and the β-D-glucuronide CHA salt (29) all gave non-diffuse colonies on agar plates. Gram-negative species grew well but the growth of some Gram-positive organisms was adversely affected by the substrates. These results showed that the 6,7-dibromo-DHN (21) is a suitable chromogenic core molecule for substrates incorporated into agar plates for the detection of Gram-negative organisms. Therefore, from a single inexpensive core molecule nucleus, i.e., DHN, we have succeeded in producing workable chromogenic enzyme substrates that are suitable for inclusion in either liquid or solid microbiological growth media. It will be appreciated by those skilled in the art that media falling between the two extremes of liquid and solid may be chosen depending on the specific application.

Example 9—Substrates Derived from DHN-6-Sulfonic Acid

DHN-6-sulfonic acid is also commercially available, most commonly as its sodium salt. As this is an unsymmetrical molecule, mono-glycosylation (or mono-derivatisation) of the aromatic ring hydroxyl groups is capable of yielding two different products. Prior to the present invention, glycosides of DHN-6-sulfonic acid were unknown. We succeeded in coupling acetobromogalactose to DHN-6-sulfonic acid by means of a phase-transfer reaction with tetrabutylammonium bromide as the catalyst. This gave a mixture of the protected di-galactoside and a protected mono-galactoside (30). The mono-galactoside (30) was isolated by column chromatography. Deprotection with sodium methoxide gave a DHN-6-sulfonic acid-β-D-galactopyranoside sodium salt (31). When tested in Columbia agar plates containing FAC (500 mg/L) at a substrate concentration of 300 mg/L it produced purple to maroon colonies after hydrolysis (Table 8). The colour was slightly different to that obtained by DHN-β-D-galactopyranoside (8) under the same conditions, but the colour was equally diffuse on agar plates.

TABLE 8

| Organism | DHN-6-sulfonic acid-β-D-galactopyranoside sodium salt 31 Colour | DHN-6-sulfonic acid-phosphate trisodium salt 32 Colour |
| --- | --- | --- |
| 1 *Escherichia coli* NCTC 10418 | + | – |
| 2 *Klebsiella pneumoniae* NCTC 9528 | – | Tr. |
| 3 *Providencia rettgeri* NCTC 7475 | + | Tr. |
| 4 *Enterobacter cloacae* NCTC 11936 | + | – |
| 5 *Serratia marcescens* NCTC 10211 | – | +/– |
| 6 *Salmonella typhimurium* NCTC 74 | – | Tr. |
| 7 *Pseudomonas aeruginosa* NCTC 10662 | – | – |
| 8 *Yersinia enterocolitica* NCTC 11176 | – | – |
| 9 *Burkholderia cepacia* NCTC 10931 | – | – |
| 10 *Acinetobacter baumannii* NCTC 19606 | – | – |
| 11 *Steptococcus pyogenes* NCTC 8306 | – | – |
| 12 *Staphylococcus aureus* (MRSA) NCTC 11939 | – | Tr. |
| 13 *Staphylococcus aureus* NCTC 6571 | – | Tr. |
| 14 *Staphylococcus epidermidis* NCTC 11047 | – | – |
| 15 *Listeria monocytogenes* NCTC 11994 | – | – |
| 16 *Enterococcus faecium* NCTC 7171 | – | – |
| 17 *Enterococcus faecalis* NCTC 775 | – | – |
| 18 *Bacillus subtilis* NCTC 9372 | – | – |
| 19 *Candida albicans* ATCC 90028 | – | – |
| 20 *Candida glabrata* NCPF 3943 | – | – |

However, the DHN-6-sulfonic acid-β-D-galactopyranoside sodium salt (31) has the benefit of being very soluble in aqueous media. It readily dissolved in water at ambient temperature (30 mg of substrate dissolved in 1 mL DI water) without the need to add any polar solvents. This is a practical advantage over other types of artificial chromogenic enzyme substrates because the polar solvents normally employed to aid solution, like DMSO, exhibit toxicity to microorganisms. DHN-6-sulfonic acid-phosphate trisodium salt (32) was also prepared and tested on agar plates at a concentration of 300 mg/L with FAC (500 mg/L) (Table 8). As with compound 31, it was very soluble water and its real value is as a substrate in liquid media.

Synthetic Methods

Materials

The glycosyl donors were all prepared by literature procedures. All other reagents and solvents were purchased from Sigma-Aldrich (Gillingham, UK), Alfa Aesar (Heysham, UK) or Univar (Widnes, UK) except where stated differently. Flash column chromatography was performed on silica gel $C_{60}$ (Fluorochem, Derbyshire, UK). TLC was carried out using pre-coated silica plates (0.2 mm, $UV_{254}$). These were developed using UV fluorescence at 254 nm and 366 nm followed by spraying with $H_2SO_4$/MeOH and heating. Mixed solvent compositions are reported as volumetric ratios, NMR spectra were recorded on a 270 MHz Joel NMR spectrometer (at 270 MHz for $^1$H and 68 MHz for $^{13}$C) or NMR spectra were recorded on a 400 MHz Joel NMR spectrometer (at 400 MHz for $^1$H and 100 MHz for $^{13}$C). All chemical shifts are quoted in ppm relative to TMS. Optical rotations were measured on an Optical Activity AA10 polarimeter. Melting points were determined with an Electrothermal AI9200 apparatus and are uncorrected. All melting points are quoted to the nearest 0.5° C. High Resolution Mass Spectroscopy (HRMS) data were obtained using the EPSRC mass spectrometry service centre (Swansea, UK).

Synthesis 1 (Reference). DHN-2',3',5-tri-O-acetyl-β-D-ribofuranoside (1)

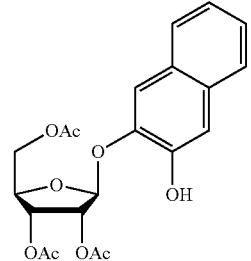

Compound 1

DHN (14.9 g) was stirred in dichloromethane (DCM) (200 mL). $BF_3$.etherate (3 mL) was added to the mixture followed by 2,3,5-tri-O-acetyl-D-ribofuranosyl-trichloroacetimidate [I. Chiu-Machado et al, J. Carb. Chem., 14, 551, (1995)] (13 g) in DCM (100 mL). After approx. 5 minutes the reaction mixture was poured into sat, aq. $NaHCO_3$ solution (300 mL) and DCM (200 mL). The DCM layer was separated and washed with sat. aq. $NaHCO_3$ solution (4×500 mL). TLC showed the reaction mixture still contained a large amount of unreacted DHN, therefore it was washed with sat. sodium carbonate (2×500 mL). TLC then showed no remaining free DHN. The DCM layer was washed with water (500 mL) before being dried over $MgSO_4$ and concentrated under reduced pressure to produce an amber foam. The isolated foam was triturated in MeOH (50 mL) and the resultant white solid harvested by filtration to give compound 1 (6.24 g, 54%), m.p. 142-144° C., $[\alpha]_D^{22}$ −69° (c 0.99 in acetone), HRMS (ESI) for $C_{21}H_{26}O_9[M+NH_4]^+$: m/z calcd 436.1602; measured: 436.1609.

Synthesis 2. DHN-β-D-ribofuranoside (2)

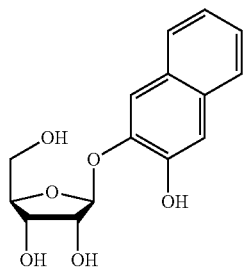

Compound 2

Compound 1 (2 g) was suspended in MeOH (6 mL), NaOMe solution in MeOH (2.17 M, 2.0 mL) was added and the reaction mixture was left at +4° C. overnight. TLC showed complete deprotection. The solution was neutralised using AcOH (0.5 mL) and the solution concentrated under reduced pressure to give a white foam. The white foam was dissolved in IMS (15 mL) and left at +4° C. overnight to crystallise. Filtration isolated compound 2 as a white solid (542 mg, 39%). m.p. 181-182° C., $[\alpha]_D^{22}$ −143° (c 0.55 in acetone/water 1:1 v/v). HRMS (ESI) for $C_{15}H_{16}O_6Na$ $[M+Na]^+$: m/z calcd 315.0839; measured: 315.0844.

Synthesis 3 (Reference). DHN-2′,3′,4′,6′-tetra-O-acetyl-β-D-glucopyranoside (3)

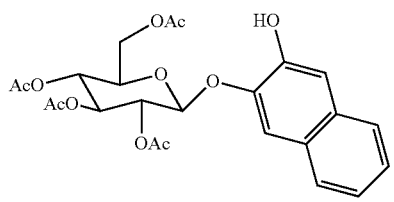

Compound 3

DHN (80.6 g, 503 mmol) and acetobromoglucose (172.6 g) were stirred in acetone (1.1 L). A solution of NaOH (20 g) in DI water (400 mL) was added in one portion. The clear orange solution was stirred overnight at room temperature. The reaction mixture was concentrated under reduced pressure until all the acetone had distilled off whereupon a gum formed in the residue. The aqueous solution was decanted off from the cream coloured gum. The gum was dissolved in DCM (1 L) and washed with sat. NaHCO$_3$ (4×1 L) and DI water (2×1 L) before being dried (MgSO$_4$) and concentrated under reduced pressure to give a yellow oil. The yellow oil was triturated in MeOH (100 mL) to give a solid that was collected by filtration. The obtained solid (63 g) was recrystallised from boiling MeOH (1 L) using charcoal (20 g) to give compound 3 (37.17 g, 18%) as a white fluffy solid. m.p. 155-156° C., $[\alpha]_D^{22}$ −24° (c 0.6 in acetone). HRMS (ESI) for $C_{24}H_{30}O_{11}N$ $[M+NH_4]^+$: m/z calcd 481.1453; measured: 481.1448. The 1H-NMR spectral data were consistent with that found in the literature.

Synthesis 4. DHN-β-D-glucopyranoside (4)

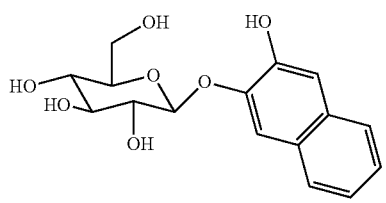

Compound 4

Compound 3 (1.5 g) was suspended in MeOH (4.5 mL) and deprotected by the method used to make compound 2. This afforded compound 4 as a white solid (930 mg, 94%). m.p. >210° C. decomp, $[\alpha]_D^{22}$ −100° (c 1.01 in water). FIRMS (ESI) for $C_{16}H_{22}O_7N$ $[M+NH_4]^+$: m/z calcd 340.1391; measured: 340.1397. The $^1$H-NMR spectral data were consistent with that found in the literature.

Synthesis 5. (Reference) DHN-2′,3′,4′,6′-tetra-O-acetyl-α-D-glucopyranoside (5)

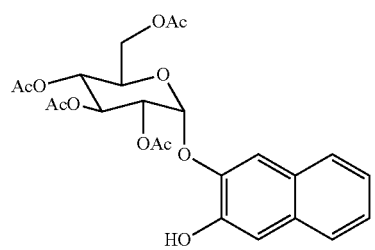

Compound 5

In a 500 mL round bottom flask, a mixture of DHN (21.8 g), HgBr$_2$ (17.3 g) and HgCN$_2$ (12.3 g) were stirred together in MeCN (250 mL) with 3 Å molecular sieves (10 g) for 10 min. Acetobromoglucose (56 g) was added and the mixture stirred at room temperature overnight. TLC then showed no remaining acetobromoglucose. The reaction mixture was filtered through Celite®, washing through with DCM (250 mL). The filtrate was washed with sat. NaHCO$_3$ (4×300 mL) and DI water (2×300 mL) before being dried (MgSO$_4$) and concentrated under reduced pressure to give a pale brown foaming oil (73.92 g). The oil was purified by flash chromatography using C$_{50}$ silica gel (1 kg), eluting with toluene/acetone 10:1 v/v, collecting fractions of 200 mL. Fractions 6-20 were concentrated under reduced pressure to produce an orange oil (30.71 g). The orange oil was triturated in IMS (50 mL) and the resultant solid (compound (3)) was collected by filtration and discarded. The filtrate from the obtained solid was concentrated under reduced pressure to give a yellow oil which was triturated in IMS (150 mL) and left at +4° C. overnight. The resultant pale yellow solid was collected by filtration (6.45 g). Recrystallisation from IMS (30 mL) using charcoal (2 g) gave compound 5 as an off-white solid (2.77 g). $[\alpha]_D^{26}$ +202° (c 0.42 in CHCl$_3$). The filtrate from the recrystallization was concentrated under reduced pressure to afford a second crop of compound 5 (1.9 g, 2.8%) $[\alpha]D^{26}$ +213° (c 0.5 in CHCl$_3$), m.p. 130-130.5° C. HRMS (ESI) for $C_{24}H_{30}O_{11}N$ $[M+NH_4]^+$: m/z calcd 508.1813; measured: 508.1815.

Synthesis 6. DHN-α-D-glucopyranoside (6)

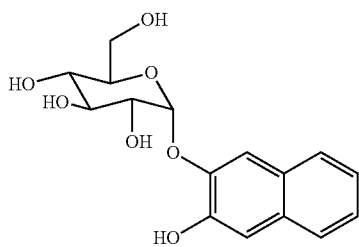

Compound 6

Compound 5 (1 g) was suspended in MeOH (3 mL) and deprotected by the method used in Synthesis 2 to make compound 2 to give compound 6 as a white fluffy solid (105 mg, 16%). m.p. 164-166° C., $[\alpha]_D^{26}$ +244° (c 0.25 in water). HRMS (ESI) for $C_{16}H_{22}O_7N$ $[M+NH_4]^+$: m/z calcd 340.1391; measured: 340.1394.

Synthesis 7. DHN-2',3',4',6'-tetra-O-acetyl-β-D-galactopyranoside (7)

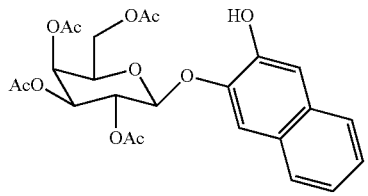

Compound 7

This compound was prepared from DHN (80.6 g) and acetobromogalactose (172.6 g) by the method used in Synthesis 3 to make compound 3. This gave compound 7 (31.5 g, 15%) as a white fluffy solid. m.p. 83-84° C., $[\alpha]D^{22}$+6° (c 1 in acetone). HRMS (ESI) for $C_{24}H_{30}O_{11}N$ $[M+NH_4]^+$: m/z calcd 508.1813; measured: 508.1805.

Synthesis 8. DHN-β-D-galactopyranoside (8)

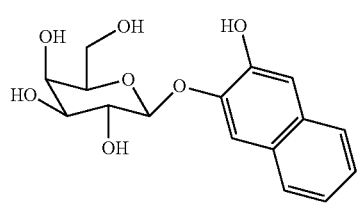

Compound 8

Compound 7 (1.5 g) was suspended in MeOH (4.5 mL) and deprotected by the method used to make compound 2 (Synthesis 2) to afford compound 8 (385 mg, 39%) as an off-white solid, m.p. >230° C. decomp, $[\alpha]_D^{22}$ −87° (c 0.62 in water). HRMS (ESI) for $C_{16}H_{22}O_7N$ $[M+NH_4]^+$: m/z calcd 340.1391; measured: 340.1397.

Synthesis 9 (Reference). DHN-2',3',4',6'-tetra-O-acetyl-α-D-galactopyranoside (9)

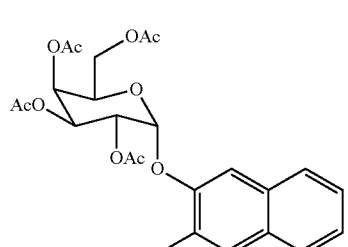

Compound 9

Compound 9 was prepared from DHN and acetobromogalactose by the method used to make the analogous glucopyranoside 5 (Synthesis 5). HRMS (ESI) for $C_{24}H_{30}O_{11}N$ $[M+NH_4]^+$: m/z calcd 508.1813; measured: 508.1814.

Synthesis 10. DHN-α-D-galactopyranoside (10)

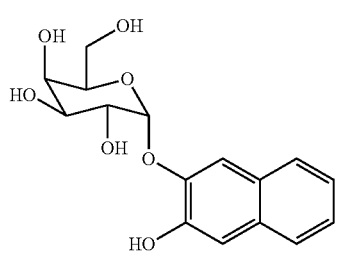

Compound 10

Compound 9 (5 g) was suspended in MeOH (15 mL) and NaOMe solution in MeOH (2.17 M, 1.5 mL) was added. After overnight reaction mixture was concentrated under reduced pressure to give a brown foam. The obtained foam was purified by flash chromatography using $C_{60}$ silica gel (220 g), eluting with DCM/MeOH 15:1 v/v, collecting fractions of 50 mL. Fractions 53-72 were combined and concentrated under reduced pressure to give compound 10 as a pink foaming solid (1.2 g, 37.5%). $[\alpha]_D^{23}$ +196° (c 0.23 in water).

Synthesis 11 (Reference). DHN-2',3',4',-tri-O-acetyl-β-D-glucuronide-6'-methyl ester (11)

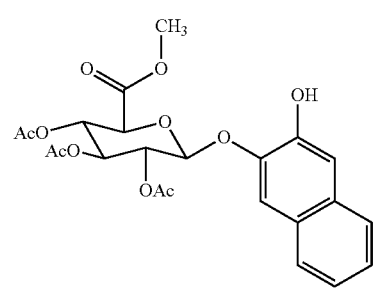

Compound 11

A mixture of DHN (34.4 g) and 1,2,3,4-tetra-O-acetyl-β-D-glucuronide-6-methyl ester (MTAG) [G. N. Bollenback et al, J. Am. Chem. Soc., 77, 3310, (1955)] (40 g) was heated in an oil bath to 120° C. on a rotary evaporator under reduced pressure until a homogeneous melt was obtained. PTSA (150 mg) in 1:1 v/v AcOH/Ac$_2$O (1 mL) was added and the mixture stirred at 120° C. on a rotary evaporator under reduced pressure for 1 hour. TLC showed some remaining MTAG, therefore PTSA (150 mg) in 1:1 v/v AcOH/Ac$_2$O (1 mL) was added and the mixture stirred at 120° C. under reduced pressure for a further 30 min. TLC then showed no remaining MTAG. The dark oil was allowed to cool to room temperature overnight before being dissolved in DCM (300 mL). The solution was washed with sat NaHCO$_3$ (4×50 mL), DI water (500 mL) and brine (500 mL) before being dried (MgSO$_4$) and concentrated under reduced pressure to give a brown foaming oil (59.1 g). The foam was purified by flash chromatography using C$_{60}$ silica gel (1 Kg), eluting with toluene/acetone 10:1 v/v, collecting fractions of 200 mL. Fractions 19-26 were combined and concentrated under reduced pressure to produce a red solid (29.66 g). The red solid was triturated in IMS (150 mL) and left at +4° C. overnight to complete crystallisation. The resultant pale yellow fluffy solid was collected by filtration to give compound 11 (12.6 g, 25%). m.p. 191-192° C. $[\alpha]_D^{23}$ −26° (c 0.5 in CHCl$_3$. HRMS (ESI) for C$_{23}$H$_{28}$O$_{11}$N [M+NH$_4$]$^+$: m/z calcd 494.1657; measured: 494.1646.

Synthesis 12a. DHN-β-D-glucuronide CHA Salt (12a)

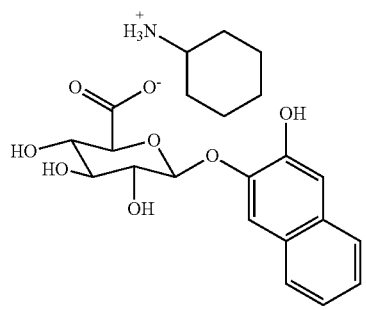

Compound 12a

Compound 11 (6.1 g) was dissolved in acetone (75 mL). A solution of NaOH (2.81 g) in DI water (37.5 mL) was added. The mixture was stirred at room temperature for 2 hours, TLC showed no remaining protected material. The solution was passed down an Amberlite®IR120 H$^+$ ion exchange resin column (50 g). The eluent containing the product was basified using cyclohexylamine (5 mL). A white precipitate formed. The mixture was left at +4° C. overnight. The white fluffy solid was collected by filtration, washing with DI water then acetone to give compound 12a as a white fluffy solid (2.8 g, 53%). m.p. 223-224° C., $[\alpha]_D^{19}$ −96° (c 0.5 in water). HRMS (ESI) for C$_{16}$H$_{16}$O$_8$ [M+H]$^+$: m/z calcd 335.0772; measured: 335.0767.

Synthesis 12b. DHN-β-D-glucuronide Sodium Salt (12b)

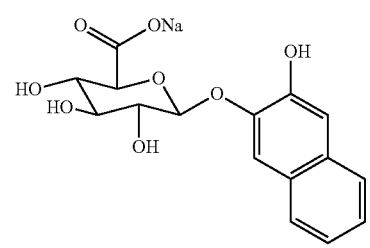

Compound 12b

Compound 11 (1.56 g) was dissolved in acetone (21 mL). A solution of NaOH (0.446 g) in DI water (1 mL) was added. The mixture was stirred at room temperature overnight, TLC showed no remaining protected material. A brown precipitate had formed in the solution. This solid was collected by filtration to give the desired compound 12b (1.16 g, 99%). m.p. 53-55° C., $[\alpha]_D^{23}$ −25° (c 0.995 in water).

Synthesis 13. DHN-β-D-glucuronide-6'-methyl ester (13)

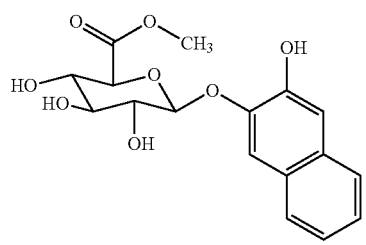

Compound 13

Compound 11 (1.0 g) was suspended in MeOH (3 mL) and NaOMe solution in MeOH (2.17 M, 0.6 mL) was added. The solid slowly dissolved and a cream precipitate began to form. The mixture was neutralised to ~pH 6-7 using AcOH (0.2 mL). The solid dissolved giving an orange solution which was concentrated under reduced pressure to give compound 13 as an orange foam (849 mg) which appeared to contain about 15% inorganic salt. $[\alpha]_D^{19}$ −100° (c 0.1 in water). HRMS (ESI) for C$_{17}$H$_{22}$O$_6$N [M+NH$_4$]$^+$: m/z calcd 368.1340; measured: 368.1339.

Synthesis 14 (Reference). DHN-N-acetyl-3',4',6'-tri-O-acetyl-β-D-glucosaminide (14)

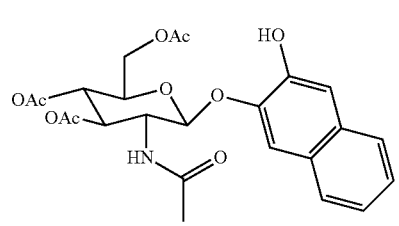

Compound 14

In a 250 mL round bottom flask a mixture of acetochloroglucosamine (30 g) and DHN (12.92 g) were stirred in acetone (1.20 mL). K$_2$CO$_3$ (21 g) was added and the mixture was heated in a water bath for 15 minutes. The reaction mixture was poured into boiling water (800 mL) and the mixture was left at room temperature for 1 hour. The resultant solid was collected by filtration and washed with water (3×800 mL) to give a brown powder (12.8 g). The obtained powder was dissolved in boiling ethyl acetate (300 mL), charcoal (5 g) was added and the reaction mixture was boiled for 10-15 minutes before being filtered through pre-washed (ethyl acetate) Celite. The clear, amber solution was concentrated under reduced pressure until crystallisation began. The resultant solid was harvested by filtration, washing with a little ethyl acetate to give compound 14 (5.5 g, 13.9%) as an off-white powder. m.p. 229-230° C., $[\alpha]_D^{27}$ −42° (c 0.5 in CHCl$_3$). HRMS (ESI) for C$_{24}$H$_{27}$O$_{10}$NNa [M+Na]$^+$: m/z calcd 512.1527; measured: 512.1526.

Synthesis 15. DHN-N-acetyl-β-D-glucosaminide (15)

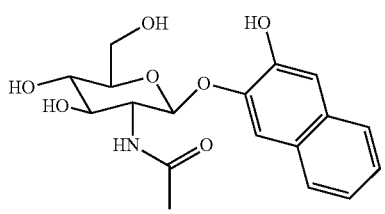

Compound 15

Compound 14 from the previous stage (1.0 g) was suspended in MeOH (3 mL) and deprotected by the method used to make compound 2 (Synthesis 2). This gave compound 15 (330 mg, 44%) as a pale orange solid. m.p. 204-205° C., $[\alpha]_D^{23}$ −10° (c 1 in MeOH). HRMS (ESI) for C$_{18}$H$_{22}$O$_7$N [M+H]$^+$: m/z calcd 364.1391; measured: 364.1388.

Synthesis 16. DHN-dicaprylate (16)

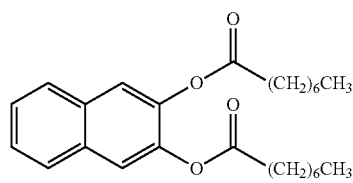

Compound 16

DHN (636 mg) was suspended in a stirred solution of octanoic acid (1.58 ml) and DCM (2 ml). Dicyclohexylcarbodiimide (DCCI) (2.2 ml) in DCM (1 ml) was added drop wise over 5 minutes. Following addition of the DCCI mixture, the DHN dissolved giving a pink coloured solution. After a few minutes of stirring, a white solid precipitated out of the solution. The reaction mixture was stirred overnight at room temperature. The white precipitate (urea) was removed by filtration and the filtrate was washed with 0.5 M NaOH solution (6×10 ml), 1% AcOH solution (1×10 ml) and finally DI water (2×10 ml). The organic layer was dried (MgSO$_4$) before being concentrated under reduced pressure to a pale orange oil. The oil was purified by dissolving in cold hexane (15 ml) with added charcoal (100 mg). After filtration and removal of the solvent under vacuum, compound 16 was obtained as a white waxy oil (970 mg, 59.2%). $^1$H NMR: (DMSO-d$_6$) δ 7.78 (2H, m), 7.63 (2H, s), 7.46 (2H, m), 2.57 (4H, t, J 7.6 Hz), 1.76 (4H, q, J 7.4 Hz), 1.46-1.25 (16H, m), 0.89 (6H, m).

Synthesis 17. DHN-phosphate Disodium Salt (17)

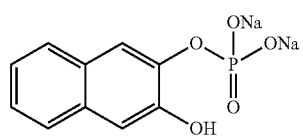

Compound 17

In a 100 mL round bottom flask MeCN (15.51 g), pyridine (6.96 g) and POCl$_3$ (13.49 g) were stirred in an ice/acetone bath. DI water (1.00 g, 55.5 mmol) was added dropwise keeping the internal temperature less than 20° C. DHN (3.2 g, 19.97 mmol) was added and the mixture was stirred for 4 hours at 2° C. The reaction mixture was poured onto ice (50 g) and 10M NaOH (50 mL) was added. The mixture was concentrated under reduced pressure to a pink solid. Following trituration in MeOH, a pink solid (salt) formed and was discarded. The filtrate containing the product and unreacted DHN was concentrated under reduced pressure to dryness. The obtained solid was triturated in IMS and a pink solid was collected by filtration. This solid was recrystallized from boiling MeOH (100 mL) containing water (25 mL) using charcoal (1 g). The MeOH was removed under reduced pressure and replaced with IMS to induce crystallisation. The resultant pink solid was collected by filtration to give the desired product (1.23 g, 21.6%). m.p. >300° C. decomp Synthesis 18. 1-Nitro-DHN-2',3',5'-tri-O-acetyl-β-D-ribofuranoside (18)

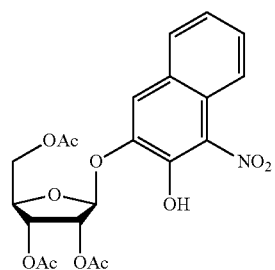

Compound 18

In a 1 L 3-neck round bottom flask, a mixture of copper (II) nitrate (60 g) and DHN-2',3',3'5'-tri-O-acetyl-β-D-ribofuranoside 1 (20.9 g) was stirred in DCM (500 mL). After rapid stirring at room temperature for 5 min. a very pale yellow colour developed. PTSA (2.0 g) was added and the solution darkened. The reaction mixture was stirred rapidly at room temperature for an additional 50 min. TLC showed a large amount of remaining starting material. More PTSA (3.0 g) was added and the reaction mixture was stirred rapidly for a further 5 hours. TLC then showed no remaining starting material. The reaction mixture was filtered to remove insoluble copper salts and the filtrate was concentrated under reduced pressure to a deep red foaming solid. The solid was purified by flash chromatography using $C_{60}$ silica gel (1 Kg), eluting with toluene/acetone 15:1 v/v, collecting fractions of 200 mL. Fractions 3-7 were combined and concentrated under reduced pressure to a yellow powder (2.61 g). The yellow powder was dissolved in boiling IMS (50 mL) and the yellow solution left at +4° C. overnight to allow crystallisation. Collected by filtration to give compound 18 as a yellow powder (2.2 g, 9.5%), m.p. 151-152° C., $[\alpha]_D^{23}$ −88° (c 0.5 in $CHCl_3$). HRMS (ESI) for $C_{21}H_{25}O_{11}N_2$ $[M+NH_4]^+$: m/z calcd 481.1453; measured: 481.1448.

Synthesis 19. 1-Nitro-DHN-β-D-ribofuranoside (19)

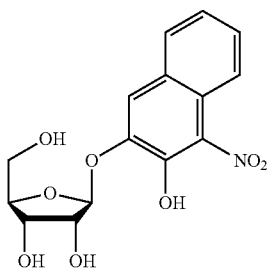

Compound 19

Compound 18 (500 mg) was suspended in MeOH (1.5 mL) and NaOMe solution in MeOH (2.17 M, 2.5 mL) was added. After overnight reaction the gel-like mixture was concentrated under reduced pressure to a red solid, triturated in IMS (10 mL) and the mixture left at +4° C. overnight. The resultant gel-like product was collected by filtration and dried under vacuum over $P_2O_5$ to give compound 19 (137.5 mg, 38%) as a yellow solid, m.p. >170° C. decomp. $[\alpha]_D^{22}$ −73° (c 0.23 in water). HRMS (ESI) for $C_{15}H_{19}O_8N_2$ $[M+NH_4]^+$: m/z calcd 355.1136; measured: 355.1140.

Synthesis 20 (Reference). 1,4,6,7-Tetrabromo-DHN (20)

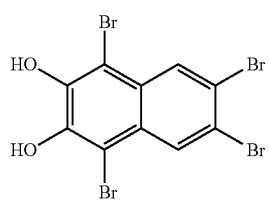

Compound 20

This was made from DHN (18 g) and bromine (23.2 mL) by the method of Zincke and Fries [loc. cit]. This produced compound 20 (36.19 g, 67%) as a very pale pink solid. m.p. 240-242° C.

Synthesis 21 (Reference). 6,7-Dibromo-DHN (21)

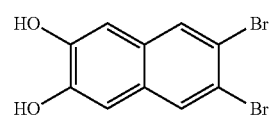

Compound 21

The title compound was made by treating 1,4,6,7-tetrabromo-DHN 20 (8 g) with tin (II) chloride (32 g) according to the conditions described by Zincke and Fries [loc. cit.]. This produced 21 (3.65 g, 68%) as a white powder, m.p. 211-213° C.

Synthesis 22 (Reference). 6,7-Dibromo-DHN-2',3', 5'-tri-O-acetyl-β-D-ribofuranoside (22)

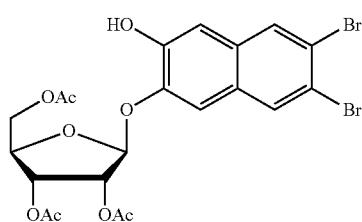

Compound 22

In a 100 mL round bottom flask, 6,7-dibromo-DHN 21 (3 g), 1,2,3,5-tetra-O-acetyl-β-D-ribofuranose (3.3 g) and 3 Å mol. sieves (1 g) were stirred in DCM (30 mL) for 10 min. $BF_3$.etherate (3 mL) was then added. After ~15 min, a thick white precipitate had formed. The reaction mixture was poured into a mixture of DCM (200 mL) and sat. $NaHCO_3$ (200 mL). The white solid dissolved. The organic layer was separated and washed with sat. $NaHCO_3$ (2×200 mL) and DI water (200 mL), dried ($MgSO_4$) and concentrated under reduced pressure to give a white solid. The solid was triturated in IMS (50 mL) and the resultant solid collected by filtration to give compound 22 (4.42 g, 81%). m.p. 185-186° C., $[\alpha]_D^{23}$ −51° (c 1 in $CHCl_3$), HRMS (ESI) for $C_{21}H_{24}O_9NBr_2$ $[M+NH_4]^+$: m/z calcd 591.9812; measured: 591.9805.

Synthesis 23. 6,7-Dibromo-DHN-β-D-ribofuranoside (23)

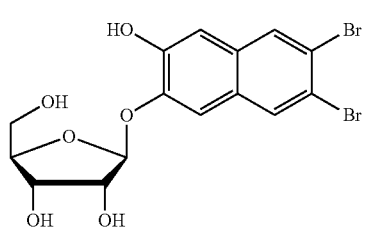

Compound 23

Compound 22 (1.0 g) was suspended in MeOH (3 mL) and deprotected by the method used to make compound 2 (Synthesis 2) to give compound 23 (697 mg, 89%), m.p.

decomp, >240° C., $[\alpha]_D^{23}$ −90° (c 0.5 in MeOH). HRMS (ESI) for $C_{15}H_{18}O_6NBr_2$ $[M+H]^+$: m/z calcd 465.9495; measured: 465.9495.

Synthesis 24 (Reference). 6,7-Dibromo-DHN-2',3',4',6'-tetra-O-acetyl-β-D-galactopyranoside (24)

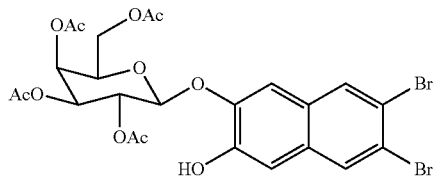

Compound 24

6,7-Dibromo-DHN 21 (6 g) and acetobromogalactose (10.23 g) were stirred in acetone (1 mL). NaOH (900 mg) in DI water (20 mL) was added in one portion. The reaction mixture was stirred overnight at room temperature at which point TLC showed no remaining acetobromogalactose. The reaction mixture was poured into DCM (500 mL) and sat. NaHCO₃ (500 mL). The DCM layer was separated and washed with sat. NaHCO₃ (6×500 mL) and DI water (500 mL), dried (MgSO₄) and concentrated under reduced pressure to give a brown oil (12.37 g). The obtained oil was purified by flash chromatography using $C_{60}$ silica gel (550 g) eluting with toluene/acetone 10:1 v/v and collecting fractions of 200 mL. Fractions 5-17 were combined and concentrated under reduced pressure to a green foaming oil (6.6 g). TLC showed that this oil contained the desired product compound 24 and unreacted 6,7-dibromo-DHN 21. The oil was dissolved in DCM (150 mL) and washed with 1M NaOH (150 mL) and DI water (150 mL) before being dried (MgSO₄) and concentrated under reduced pressure to give compound 24 (4.6 g, 37%) as a pale green foaming solid, $[\alpha]_D^{19}$ +20° (c 0.5 in acetone). HRMS (ESI) for $C_{24}H_{28}O_{11}NBr_2$ $[M+NH_4]^+$: m/z calcd 664.0024; measured: 664.0023.

Synthesis 25.
6,7-Dibromo-DHN-β-D-galactopyranoside (25)

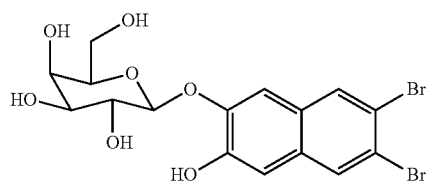

Compound 25

Compound 24 (4.35 g) was deprotected in a similar manner to that used to make compound 2 (Synthesis 2) except that the solution was neutralised with Amberlite® IR120H⁺ resin. The powder was purified by recrystallization from MeOH/water 1:1 v/v (300 mL) to give compound 25 (1.89 g, 59%) as a white solid. m.p. 256-257° C., $[\alpha]_D^{25}$ −64° (c 0.25 in acetone/water 1:1 v/v). HRMS (ESI) for $C_{16}H_{16}O_7Br_2$ $[M+H]^+$: m/z calcd 476.9190; measured: 476.9203.

Synthesis 26 (Reference). 6,7-Dibromo-DHN-2',3',4',6'-tetra-O-acetyl-β-D-glucopyranoside (26)

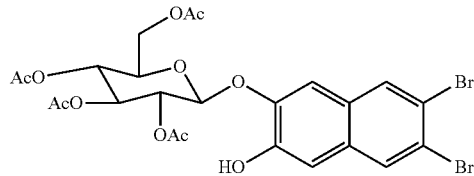

Compound 26

This was made from 6,7-Dibromo-DHN 21 (6 g) and acetobromoglucose (10.23 g) by essentially the same method used for the analogous galactopyranoside 24 (Synthesis 24). The title compound 26 was obtained as a white solid (3.16 g, 25%). m.p. 166-167° C., $[\alpha]_D^{25}$ −28° (c 0.5 in acetone). HRMS (ESI) for $C_{24}H_{28}O_{11}NBr_2$ $[M+NH_4]^+$: m/z calcd 664.0024; measured: 664.0025.

Synthesis 27.
6,7-Dibromo-DHN-β-D-glucopyranoside (27)

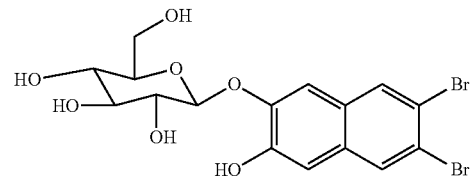

Compound 27

Compound 26 (3 g) was suspended in MeOH (8 mL) and deprotected by the addition of NaOMe solution in MeOH (2.17 M, 3 mL). Work-up gave compound 27 (2.04 g, 92%) as a very pale green solid. m.p. decomp. >290° C., $[\alpha]_D^{25}$ −168° (c 0.25 in water). HRMS (ESI) for $C_{16}H_{15}O_7Br_2$ $[M+H]^+$: m/z calcd 476.9190; measured: 476.9186.

Synthesis 28 (Reference). 6,7-Dibromo-DHN-2',3',4'-tri-O-acetyl β-D-glucuronide-6'-methyl ester (28)

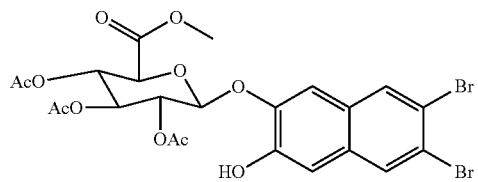

Compound 28

α-D-2,3,4-Tri-O-acetyl-β-D-glucuronyl-trichloroacetimidate-6-methyl ester (10 g) and 6,7-dibromo-DHN 21 (6 g) were stirred in DCM (100 mL). BF₃.etherate (~200 µL) was added. The reaction mixture was stirred at room temperature for 30 min. before being poured into a mixture of DCM (500 mL) and sat. NaHCO₃ (500 mL). The DCM layer was separated and washed with sat. NaHCO₃ (4×500 mL) and DI water (500 mL), dried (MgSO₄) and concentrated under reduced pressure to give a pink solid. The obtained solid was triturated in IMS (100 mL) and left at +4° C. overnight. The resultant solid was harvested by filtration to give compound 28 (2.89 g, 24%) as a white solid. m.p. 176-177° C., $[\alpha]_D^{25}$ −16° (c 0.25 in acetone). HRMS (ESI) for $C_{23}H_{26}O_{11}NBr_2$ $[M+NH_4]^+$: m/z calcd 649.9867; measured: 649.9868.

Synthesis 29. 6,7-Dibromo-DHN-β-D-glucuronide CHA Salt (29)

Compound 29

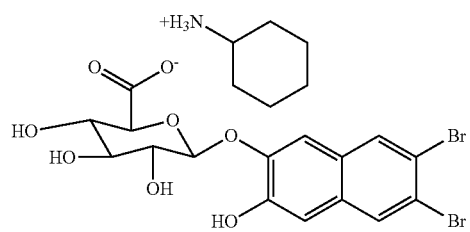

Compound 28 (2.5 g) was deprotected with NaOH (870 mg) in a mixture of DI water (11.5 mL) and acetone (23 mL). Work-up as for compound 12a with pro-rata quantities gave compound 29 as a white solid (2.16 g, 95%). m.p. 221-224° C., $[\alpha]_D^{25}$ −159° (c 0.25 in water). HRMS (ESI) for $C_{16}H_{13}O_8Br_2$ $[M+H]^+$: m/z calcd 490.8983; measured: 490.8976.

Synthesis 30 (Reference). DHN-6-sulfonic acid-2',3',4',6'-tetra-O-acetyl-β-D-galactopyranoside sodium salt (30)

Compound 30

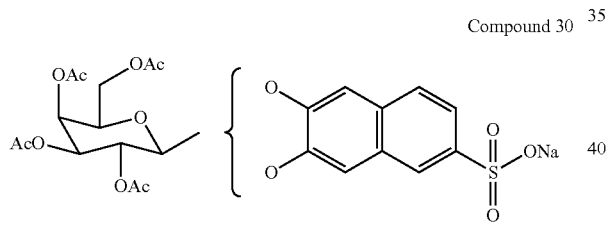

DHN-6-sulfonic acid sodium salt (5 g) was dissolved in a solution of NaOH (850 mg) in DI water (150 mL). Acetobromogalactose (7.06 g), tetrabutylammonium bromide (8.75 g) and DCM (8.7 g) were added and the two-phase reaction mixture was stirred overnight at ambient temperature. TLC analysis showed no remaining acetobromogalactose. The reaction mixture was diluted with additional DCM (100 mL) and the organic layer was separated before being washed with DI water (300 mL), dried (MgSO₄), and concentrated under reduced pressure to an oil (15.83 g). The isolated oil was purified by flash chromatography using C60 silica (600 g), eluting with DCM/MeOH. Fractions 7-20 were combined and concentrated under reduced pressure to an oil which was triturated in ethyl acetate (30 mL). The resultant white solid was collected by filtration to give protected mono-galactoside 30 (4.77 g, 49.68%). m.p. 131-133° C., $[\alpha]_D^{23}$ +5° (c 0.592 in acetone). ¹H NMR (DMSO-d₆): δ 9.73 (1H, s), 7.90 (1H, s), 7.55 (1H, dd), 7.45 (1H, m), 7.40 (1H, s), 7.16 (1H, s), 5.47 (1H, d), 5.32 (1H, broad s), 5.25 (2H, m), 4.43 (1H, m), 4.10 (1H, m) 2.13, 1.99, 1.96, 1.91 (4×3H, 4×s). ¹H NMR spectroscopy confirmed the obtained solid was the mono-galactoside, although which of the two possible isomers could not be determined from the NMR data.

Synthesis 31. DHN-6-sulfonic acid-β-D-galactopyranoside sodium salt (31)

Compound 31

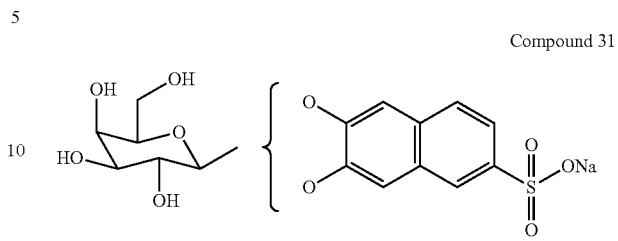

Compound 30 (1 g) was suspended in MeOH (3 mL), 2.17 M NaOMe (0.5 mL) was added. Additional 2.17 M sodium methoxide (3 mL, 3.3 mmol) was added to aid crystallisation of the sodium salt. After complete deprotection (by TLC) the mixture was concentrated under reduced pressure and triturated in IMS (10 mL). The solid was collected by filtration and washed with a little IMS to afford compound 31 (462 mg, 62%). m.p. >230° C. decomp, $[\alpha]D^{23}$ −73° (c 0.26 in water). ¹H NMR (DMSO-d₆): δ 7.45 (1H, s), 7.27 (1H, d), 7.09 (1H, s). 6.98 (1H, dd), 6.41 (1H, s), 4.55 (1H, d), 363 (1H, d), 3.52 (3H, m), 3.31 (2H, m). ¹H NMR spectroscopy confirmed the obtained solid was the mono-galactoside, although which of the two possible isomers could not be determined from the NMR data.

Synthesis 32. DHN-6-sulfonic acid-phosphate trisodium salt (32)

Compound 32

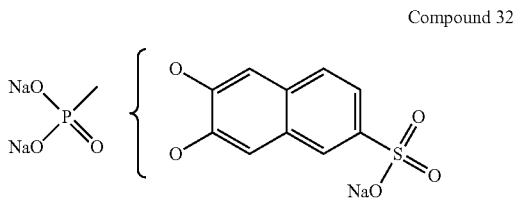

In a 100 mL round bottom flask MeCN (15.51 g), pyridine (6.96 g) and POCl₃ (13.49 g) were stirred in an ice/acetone bath. DI water (1.00 g, 55.5 mmol) was added dropwise keeping the internal temperature less than 20° C. DHN-6-sulfonic acid sodium salt (5.24 g) was added and the mixture was stirred for 4 hours at 2° C. The reaction mixture was poured onto ice (100 g) and 10M NaOH (35 mL) was added. The mixture was concentrated under reduced pressure to give an orange solid which was triturated in MeOH (200 mL). The resultant solid (33.4 g) was mainly salt and was discarded. The filtrate was concentrated under reduced pressure to an orange solid (4.44 g). This was dissolved in hot DI water (20 mL), filtered, and IMS (200 mL) was added to the clear brown filtrate. A brown oil separated out of the mixture. After decanting the IMS/water solution from the oil, a pale cream precipitate formed in this solution. It was removed by filtration, and this filtrate was now recombined with the previously isolated brown oil. Concentration of this mixture under reduced pressure gave a brown foam. This foam was heated with MeOH (75 mL) in an ultrasonic bath; a fine hygroscopic brown solid was removed by filtration and the clear brown filtrate was concentrated under reduced pressure to a solid. Trituration of the solid in IMS (30 mL) gave a mixture of isomers of title compounds (32) as an off-white solid (1.17 g, 14.7%). m.p. >400° C.

The invention claimed is:

1. A method of detecting target enzyme activity in a liquid medium comprising the steps:
   a) contacting, in the liquid medium; a water soluble iron compound and an enzyme substrate represented by formula I with a substance suspected of containing or producing the target enzyme

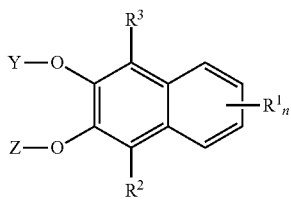

wherein Y is an enzyme cleavable group;
   Z is H, a metal cation or non-metal cation, acyl or the same enzyme cleavable group as Y;
   $R^2$ and $R^3$ are each independently selected from the group consisting of H, OH, $C_1$-$C_8$ alkyl, $C_2$-$C_{24}$ acyl, halogen and nitro, provided that if Z is H or a salt, then $R^2$ must not be OH;
   $R^1$ is $C_1$-$C_8$ alkyl, halogen, OH, $NO_2$, $C_2$-$C_{24}$ acyl, or —$SO_3X$, where X is H, a meta cation or a non-metal cation;
   n is 0-4;
   such that a product of enzymatic substrate cleavage is capable of chelating the iron ion of the water soluble iron compound, thereby forming a colored compound; and
   b) detecting the presence of the colored compound.

2. The method according to claim 1, wherein n is 0.

3. The method according to claim 1, wherein n is 1 and $R^1$ is $SO_3X$ where X is H or $M^{p+}_{1/p}$, where p is 1, 2 or 3 and M is a metal.

4. The method according to claim 1, wherein n is 1 or 2 and each $R^1$ is halogen.

5. The method according to claim 4, wherein $R^2$ and $R^3$ are both H.

6. The method according to claim 1, wherein Z is H.

7. The method according to claim 1, wherein Y is an O-glycosyl, a $C_{2-24}$ acyl, a phosphate, a sulfate or a peptidyl group.

8. The method according to claim 1, wherein Y is an O-glycosyl group derived from a monosaccharide.

9. The method according to claim 1, where $R^2$ is H and $R^3$ is OH.

10. The method according to claim 1, wherein $R^2$ is $NO_2$ and $R^3$ is H.

11. The method according to claim 1, wherein the substance is a sample suspected of containing microbes.

12. The method according to claim 11, wherein the microbes include bacteria.

13. The method according to claim 11, wherein step a) includes a step of incubating the substance in a liquid medium for microbial growth under microbial growth conditions for a microbial growth period.

14. The method according to claim 13, wherein the liquid medium further contains an additional microbial enzyme substrate comprising a chromogen, the cleavage product of which is different than the cleavage product of the enzyme substrate of formula I.

15. The method according to claim 1, wherein the concentration of the water soluble iron compound in the liquid medium is at least 50 mg/L.

* * * * *